(12) United States Patent
Camp et al.

(10) Patent No.: US 8,651,403 B2
(45) Date of Patent: Feb. 18, 2014

(54) ANHYDROUS AMMONIA TREATMENT FOR IMPROVED MILLING OF BIOMASS

(75) Inventors: Carl E. Camp, Wilmington, DE (US); Jelena Cirakovic, Towson, MD (US); Bruce A. Diner, Chadds Ford, PA (US); Janine Fan, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 391 days.

(21) Appl. No.: 13/185,572

(22) Filed: Jul. 19, 2011

(65) Prior Publication Data

US 2012/0187228 A1  Jul. 26, 2012

Related U.S. Application Data

(60) Provisional application No. 61/366,231, filed on Jul. 21, 2010.

(51) Int. Cl.
  *B02C 25/00*  (2006.01)

(52) U.S. Cl.
  USPC ............................................................ 241/30

(58) Field of Classification Search
  USPC ............................................................ 241/30
  See application file for complete search history.

(56) References Cited

U.S. PATENT DOCUMENTS

| | | | |
|---|---|---|---|
| 7,708,214 B2 * | 5/2010 | Medoff | 241/28 |
| 7,781,191 B2 | 8/2010 | Dunson, Jr. et al. | |
| 7,910,338 B2 | 3/2011 | Hennessey et al. | |
| 7,932,063 B2 | 4/2011 | Dunson, Jr. et al. | |
| 7,998,713 B2 | 8/2011 | Dunson, Jr. et al. | |
| 2008/0008783 A1 | 1/2008 | Dale | |
| 2009/0042259 A1 | 2/2009 | Dale et al. | |
| 2010/0159516 A1 | 6/2010 | Diner et al. | |
| 2010/0159517 A1 | 6/2010 | Diner et al. | |
| 2010/0159520 A1 | 6/2010 | Diner et al. | |
| 2010/0159521 A1 | 6/2010 | Cirakovic et al. | |
| 2010/0159522 A1 | 6/2010 | Cirakovic | |

OTHER PUBLICATIONS

Kabeya, Hiroshi et al., Shikoku Kogyo Gijutsu Shikensho Kenkyu Hokoku, Chapter 4: Chemical and Physical Pretreatments for Enhancement of the Enzymatic Hydrolysis of Thermomechanical Pulp, 1993, pp. 42-90, vol. 24.

Chundawat, Shishir et al., Effect of Particle Size Based Separation of Milled Corn Stover on AFEX Pretreatment and Enzymatic Digestibility, Biotechnology and Bioengineering, Feb. 1, 2007, pp. 219-231, vol. 96, No. 2.

Dale, Bruce E. et al., Extrusion Processing for Ammonia Fiber Explosion (AFEX), Applied Biochemistry and Biotechnology, 1999, pp. 35-45, vol. 77-79.

Taylor, Frank et al., Corn-Milling Pretreatment and Anhydrous Ammonia, Applied Biochemistry and Biotechnology, 2003, pp. 141-148, vol. 104.

Bals, Bryan et al., Evaluation of ammonia fibre expansion (AFEX) pretreatment for enzymatic hydrolysis of switchgrass harvested in different seasons and locations, Biotechnology and Biofuels, 2010, pp. 1-11, vol. 3, No. 1.

Banerjee, Goutami et al., Synthetic Enzyme Mixtures for Biomass Deconstruction: Production and Optimization of a Core Set, Biotechnology and Bioengineering, Aug. 1, 2010, pp. 707-720, vol. 106.

* cited by examiner

Primary Examiner — Faye Francis

(57) ABSTRACT

Mechanical milling of biomass as a pretreatment to render the biomass readily saccharifiable requires high energy input. Preceding mechanical milling by treatment with anhydrous ammonia was found to greatly reduce the energy requirement for fine milling, providing a more economical pretreatment process for commercial use.

16 Claims, 23 Drawing Sheets

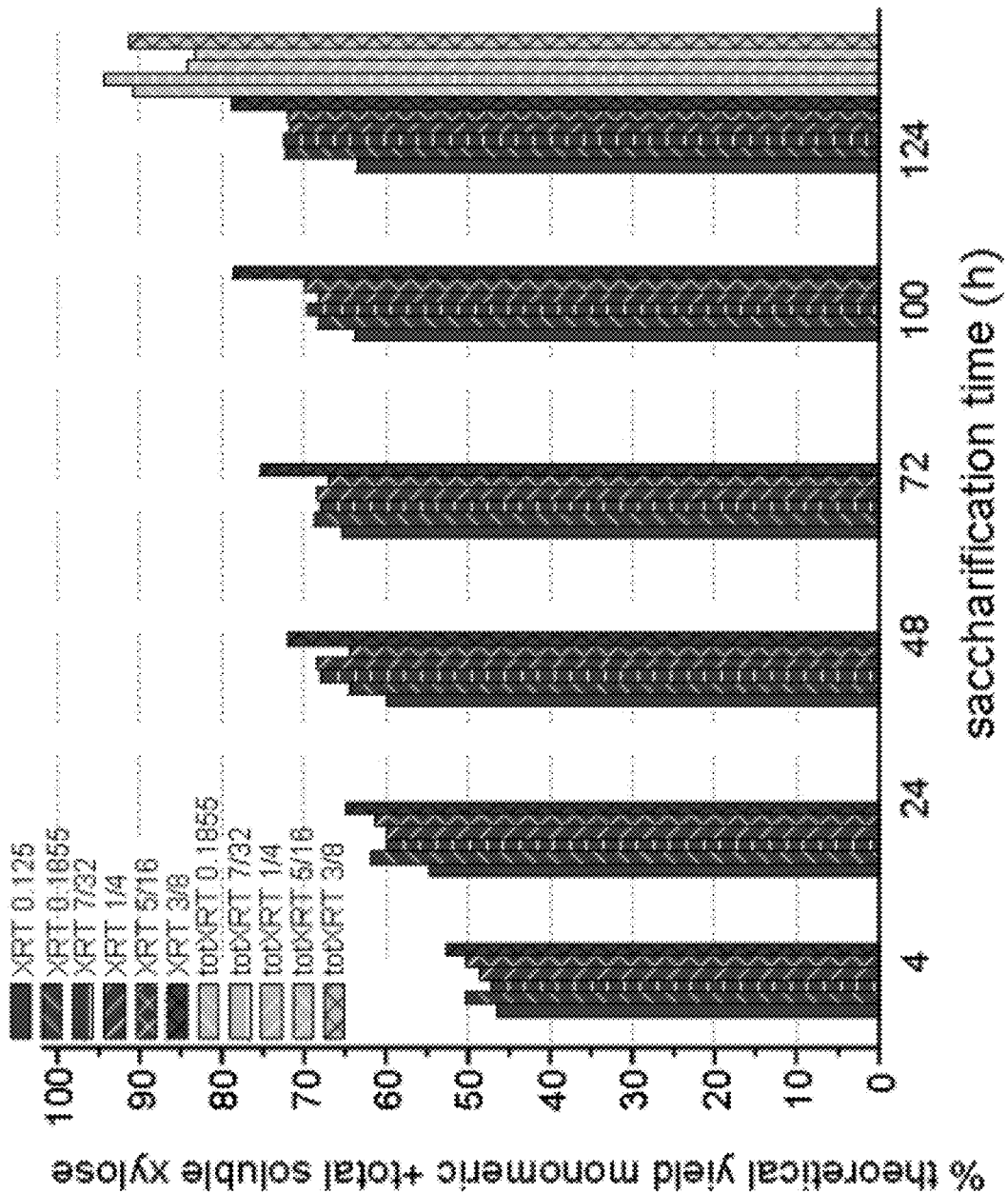

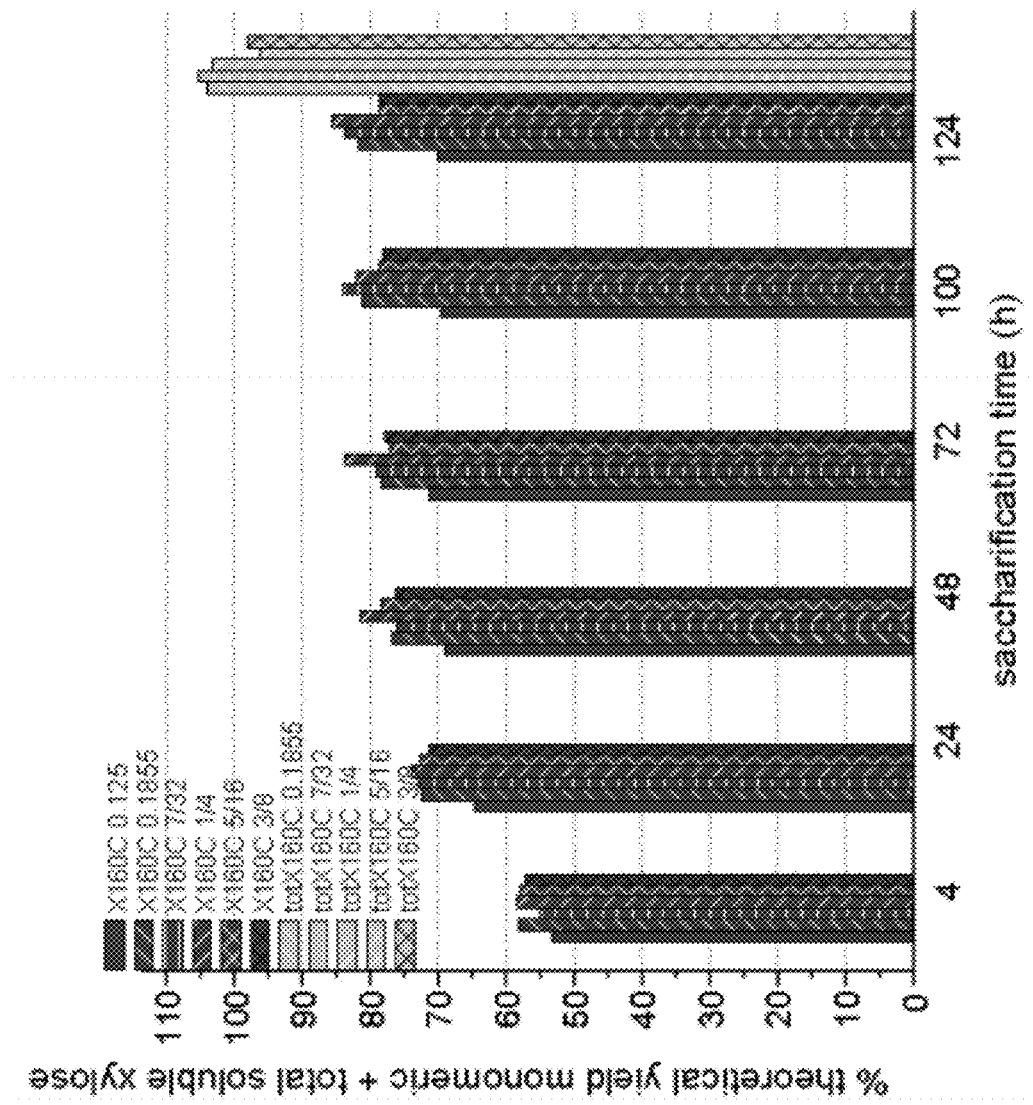

ANHYDROUS AMMONIA TREATMENT FOR IMPROVED MILLING OF BIOMASS

This application claims the benefit of U.S. Provisional Application 61/366,231 filed Jul. 21, 2010, incorporated by reference in its entirety.

FIELD OF THE INVENTION

Methods for producing readily saccharifiable lignocellulosic biomass are provided. Specifically, biomass is pretreated using anhydrous ammonia followed by milling or other mechanical disruption means. Anhydrous ammonia treatment reduces the energy of milling that is required to provide readily saccharifiable material and increases the overall rate of the pretreatment and saccharification process.

BACKGROUND OF THE INVENTION

Lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Lignocellulosic feedstocks and wastes, containing the carbohydrate polymers cellulose, and hemicellulose, as well as lignin, are generally treated by a variety of chemical, mechanical and enzymatic means to release primarily hexose and pentose sugars, which can then be fermented to useful products.

Pretreatment methods are used to make the carbohydrate polymers, or polysaccharides, of lignocellulosic biomass more readily accessible to cellulolytic enzymes used in saccharification. A major impediment to cellulolytic enzyme digestion of polysaccharide is the presence of lignin, which is a barrier that limits the access of the enzymes to their substrates, and provides a surface to which the enzymes bind non-productively. In addition, the crystallinity of cellulose microfibrils restricts enzyme access providing an obstacle to saccharification. Pretreatment methods that attempt to overcome these challenges include: steam explosion, hot water, dilute acid, ammonia fiber explosion, alkaline hydrolysis (including ammonia recycled percolation), oxidative delignification, organosolv, and ozonation. Costs of chemicals, chemical recovery, energy inputs, and capital equipment make many methods not amenable to commercial production.

Biomass pretreatment using low amounts of aqueous ammonia and a high solids concentration is disclosed in commonly owned U.S. Pat. No. 7,932,063. US 20080008783 discloses treatment of biomass, which has been ground and which contains varying moisture contents, with anhydrous ammonia in the liquid or vapor state, and/or concentrated ammonia:water mixtures in the liquid or vapor state, to obtain a mixture in which the ratio of ammonia to dry biomass is between about 0.2 to 1 and 1.2 to 1, and the water to dry biomass ratio is between about 0.2 to 1.0 and 1.5 to 1. The temperature is maintained between about 50° C. and 140° C. and the pressure is rapidly released by releasing ammonia from the vessel to form a treated biomass.

Milling, where biomass is ground, has been used as a non-chemical pretreatment, or used in combination with ozonolysis ((Kabeya et al. (1993) Shikoku Kogyo Gijutsu Shikensho Kenkyu Hokoku 24:42-90).

There remains a need for alternative efficient, low cost lignocellulosic biomass pretreatment processes that prepare biomass for saccharification.

SUMMARY OF THE INVENTION

The invention provides a process for preparing biomass so that it may be readily saccharified to produce sugars for use in fermentation by a biocatalyst. The method involves the application of anhydrous ammonia to the biomass prior to the application of mechanical energy for the purpose of mechanical disruption and reduction of particle sized of the biomass. It has been unexpectedly found that this sequence of treatment by anhydrous ammonia followed by mechanical disruption has the beneficial effect of reducing the time and energy required for particle size reduction and results in a higher rate of production of fermentable sugars during saccharification thus enhancing the rate of the entire process.

Accordingly, the invention provides a process for producing readily saccharifiable biomass comprising:
  a) providing lignocellulosic biomass;
  b) contacting the biomass of (a) with anhydrous ammonia to produce ammonia-treated biomass; and
  c) disrupting the ammonia-treated biomass of (b) by applying mechanical energy through a mechanical disruption means to produce a pretreated biomass which is readily saccharifiable;
wherein the pretreated biomass comprises an amorphous cellulose component and;
wherein the percentage of the amorphous cellulose component in the pretreated biomass is higher as compared with the percentage of the amorphous cellulose component in a pretreated biomass not contacted with anhydrous ammonia and disrupted with the same level of mechanical energy as in (c).

Pretreated biomass of the invention typically will have a particle size of less than about 0.1 mm and the energy needed to effect the disruption of the biomass is generally 4-10 fold less when anhydrous ammonia is used prior to the disruption.

DETAILED DESCRIPTION

Figure 1A:
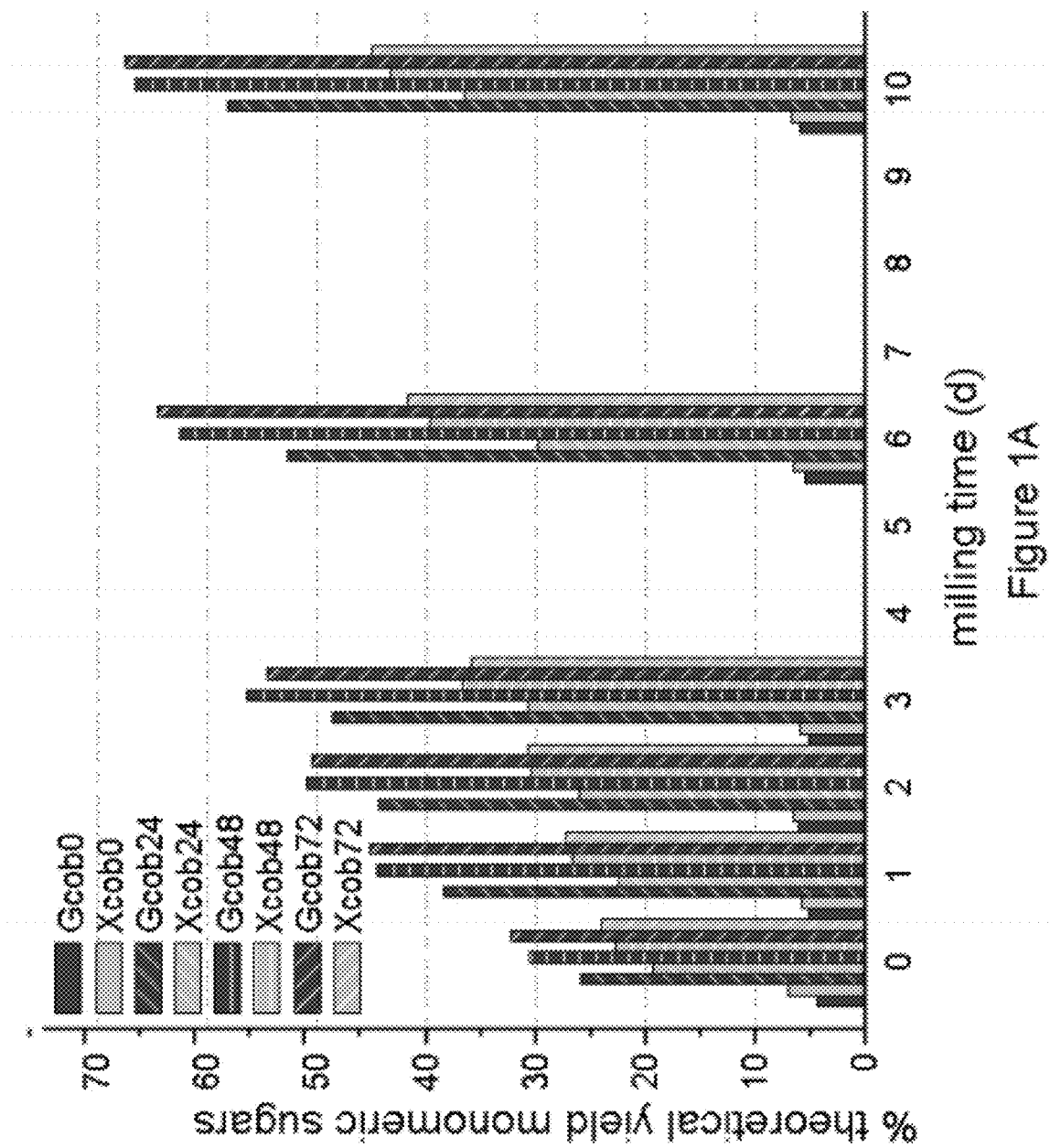
FIG. 1 shows graphs of percent of theoretical yields of monomeric glucose (G) and xylose (X) in samples saccharified (at 14% solids loading) for different times (0, 24, 48, 72 hours), plotted against the time the biomass was milled with 1 cm diameter Yttrium doped $ZrO_2$ beads (0, 1, 2, 3, 6, 10 days) for 1 mm knife milled untreated cob in (A) and 1 mm knife milled untreated late winter/early spring harvested switchgrass (swg) in (B).

The present invention relates to pretreatment of lignocellulosic biomass to prepare the biomass for producing fermentable sugars during saccharification. The biomass is treated with a mechanical disruption means, with prior or concurrent treatment of anhydrous ammonia which reduces the amount of energy needed to produce a readily saccharifiable biomass product. Sugars produced from biomass treated as disclosed herein are used in fermentation using a biocatalyst to produce desired target products.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

"Anhydrous ammonia" refers to ammonia gas that is dry and not in an aqueous medium.

"Room temperature" and "ambient" when used in reference to temperature refer to any temperature from about 15° C. to about 25° C.

"Fermentable sugars" refers to a sugar content primarily comprising monosaccharides and some oligosaccharides that can be used as a carbon source by a microorganism in a fermentation process to produce a target product.

"Monomeric sugars" or "simple sugars" consist of a single pentose or hexose unit, e.g., glucose.

"Lignocellulosic" refers to material comprising both lignin and cellulose. Lignocellulosic material may also comprise hemicellulose.

"Cellulosic" refers to a composition comprising cellulose.

"Dry weight of biomass" refers to the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard). Dry weight of biomass is synonymous with dry matter content of biomass.

"Substantially dry" in reference to biomass refers to biomass having a dry matter content of at least about 85%, or moisture content of about 15% or less.

"Biomass" and "lignocellulosic biomass" will be used interchangeably and refers to any lignocellulosic material, including cellulosic and hemicellulosic material, for example, bioenergy crops, agricultural residues, municipal solid waste, industrial solid waste, yard waste, wood, forestry waste, and combinations thereof, and as further described below. Biomass has a carbohydrate content that comprises polysaccharides and oligosaccharides and may also comprise additional components, such as protein and/or lipid.

"Saccharification" and "saccharifying" refer to the production of fermentable sugars from polysaccharides by the action of acids, bases, or hydrolytic enzymes. Production of fermentable sugars from pretreated biomass occurs by enzymatic saccharification by the action of cellulolytic and hemicellulolytic enzymes.

"Polysaccharide" refers to any of a class of carbohydrates formed by repeating units linked together by glycosidic bonds, or a complex carbohydrate composed of a chain of monosaccharides joined together by glocosidic bonds. Polysaccharides have the general formula $C_x(H_2O)_y$.

"Pretreating biomass" or "biomass pretreatment" as used herein refers to subjecting native or preprocessed biomass to chemical, physical, or biological action, or any combination thereof, rendering the biomass more susceptible to enzymatic saccharification or other means of hydrolysis prior to saccharification. For example, the methods claimed herein may be referred to as pretreatment processes that contribute to rendering biomass more accessible to hydrolytic enzymes for saccharification.

"Fine-milled material" as used herein refers to material that has reduction in particle size, where the particle size is less than 0.1 mm.

The term "mechanical disruption means" refers to methodologies for the mechanical disruption of biomass that results in the reduction of particle size. Typical mechanical disruption means will include, but will not be limited to, attritor milling, hammer milling, ball milling, bead milling, vibratory ball milling, vibratory rod milling, jet milling, pin milling, turbine milling, air classifier milling, roll milling and planetary ball milling.

The term "amorphous component" or "amorphous cellulose component" when used in the context of pretreated biomass refers to the non-crystalline cellulose fraction of the biomass typically determined by wide-angle X-ray diffraction measurements for crystallinity.

"Coarse size reduced" as used herein refers to reduced size of pieces or particles of material where the size is greater than 0.1 mm.

"Readily saccharifiable biomass" as used herein refers to biomass that produces high sugar yields in saccharification. High sugar yields following saccharification of at least about 70% of theoretical yield of glucose and at least about 60% of theoretical yield of xylose, or greater, are indicative of a readily saccharifiable pretreated biomass.

"Hydrolysate" refers to the liquid in contact with the lignocellulose biomass which contains the products of hydrolytic reactions acting upon the biomass (either enzymatic or not), in this case monomeric and oligomeric sugars.

"Enzyme consortium" or "saccharification enzyme consortium" is a collection of enzymes, usually secreted by microorganisms, which in the present case will typically contain one or more cellulases, xylanases, glycosidases, ligninases and feruloyl esterases.

As used herein "pounding" refers to impacting with force.

The term "target product" refers to any product that is produced by a microbial production host cell in a fermentation. Target products may be the result of genetically engineered enzymatic pathways in host cells or may be produced by endogenous pathways. Typical target products include but are not limited to acids, alcohols, alkanes, alkenes, aromatics, aldehydes, ketones, biopolymers, proteins, peptides, amino acids, vitamins, antibiotics, and pharmaceuticals.

Lignocellulosic Biomass

Biomass used in the present method is lignocellulosic, which contains polysaccharides such as cellulose and hemicellulose, and lignin. Polysaccharides of biomass may also be called glucans and xylans. Types of biomass that may be used include, but are not limited to, bioenergy crops, agricultural residues, municipal solid waste, industrial solid waste, sludge from paper manufacture, yard waste, wood and forestry waste. Examples of biomass include, but are not limited to corn cobs, corn husks, corn stover, grasses, wheat straw, barley straw, oat straw, canola straw, hay, rice straw, switchgrass, miscanthus, cord grass, reed canary grass, waste paper, sugar cane bagasse, sorghum bagasse or stover, soybean stover, components obtained from milling of grains, trees, branches, roots, leaves, wood chips, sawdust, shrubs and bushes, vegetables, fruits, flowers and animal manure. Biomass may include other crop residues, forestry wastes such as aspen wood, other hardwoods, softwood and sawdust; and post-consumer waste paper products; and fiber process residues such as corn fiber, beet pulp, pulp mill fines and rejects; as well as other sufficiently abundant lignocellulosic material.

Biomass that is particularly useful for the invention includes biomass that has a relatively high carbohydrate content, is relatively dense, and/or is relatively easy to collect, transport, store and/or handle.

The lignocellulosic biomass may be derived from a single source, or biomass can comprise a mixture derived from more than one source; for example, biomass could comprise a mixture of corn cobs and corn stover, or a mixture of stems or stalks and leaves.

The biomass may be used directly as obtained from the source, or may be subjected to some preprocessing, for example, mechanical energy may be applied to the biomass to reduce size or moisture. Size reduction may be performed using methods that produce coarse size reduced material, where the obtained size is greater than 0.1 mm. Methods that may be used include knife milling, crushing, shredding, chopping, disc refining, and coarse hammer milling. This type of size reduction may be performed before, during or after treatment with anhydrous ammonia. Drying may be by any conventional means such as by using a drying oven, rotary dryer, flash dryer, or superheated steam dryer. In addition, air drying may be sufficient for reaching a desired biomass moisture content that is less than about 15%, preferably between about 7% and 10% as described below. For use in the present method it is desirable that the biomass has a dry matter content of at least about 85, 90, or 93 weight percent.

Biomass Pretreatment

Lignocellulosic biomass is typically treated prior to saccharification to prepare it for hydrolysis. This pretreatment improves the hydrolysis, or release of sugars, during saccharification. Sugar release, primarily glucose and xylose, from the polysaccharides of biomass is difficult due to the presence of lignin that constitutes a physical barrier and also a surface for non-productive binding of saccharification enzymes. In addition, the crystallinity and tight packing of cellulose microfibrils restricts access of the enzymes.

Ball milling alone can be used as a biomass pretreatment to improve saccharification, eliminating the use of acidic or basic pretreatment chemicals. However, for ball milled biomass to generate high sugar yields in saccharification, ball milling application with high energy input is needed. The mechanical energy required for ball milling to allow high monomeric sugar yields upon saccharification is extensive, such that this pretreatment method by itself is not economical. For example, the energy used for ball-milling exceeds the energy contained in a biomass sample after 5 days of milling.

In the present method, lignocellulosic biomass is contacted with anhydrous ammonia prior to disruption using a mechanical disruption means to produce fine-milled material. Optionally the biomass may be contacted with the anhydrous ammonia concurrent with the mechanical disruption. Applicants have found that by treating biomass with anhydrous ammonia prior to using ball or attritor milling to produce fine-milled material, the mechanical energy input for ball milling pretreatment to obtain a readily saccharifiable pretreated biomass product is greatly reduced. Readily saccharifiable biomass is one that produces high sugar yields in saccharification. High sugar yields of at least about 70% of theoretical yield of glucose and at least about 60% of theoretical yield of xylose, or greater, are indicative of a readily saccharifiable pretreated biomass.

When applied following anhydrous ammonia treatment, the mechanical energy needed for fine milling is at least about four-fold less and may be about 6-fold to about 10-fold less to produce an amount of sugars following saccharification that is an equivalent amount to that from saccharification of milled biomass with the anhydrous ammonia treatment omitted. The amount of reduction in mechanical energy is variable and depends on factors such as the type of biomass, moisture content, strength of anhydrous ammonia treatment (including factors such as concentration, temperature, time), and type of mechanical energy application method. The reduction in mechanical energy may be at least about four-fold, five-fold, six-fold, seven-fold, eight-fold, nine-fold, 10-fold, or more.

In general the amount of time needed to disrupt the biomass may be correlated to the energy required to effect the disruption process. For example, it has been determined that Fall harvested switchgrass has an energy content of 18.5 gigajoules per ton (GJ/ton). A typical milling run performed herein using a conventional ball mill uses about 5 grams of biomass comprising $9.25 \times 10^4$ joules (J). For this sample, where the milling occurs over a 10 day period, approximately $2.2 \times 10^5$ J (energy delivered to milled material) will be consumed. So for example where the milling occurs over 19 hours, $1.74 \times 10^4$ J is consumed which equates to 19% of the energy content of the biomass. Similarly where the milling occurs over a 5 hour period $4.58 \times 10^3$ J or 5% of the energy content of the biomass is consumed. The amount of energy reduction achieved from using the ammonia pretreatment may also be measured directly. For example, milling may occur using an attritor mill. This mill delivers about 60× the power of the conventional ball mill. Running the attritor mill on 0.5 kg of biomass for 5 minutes, the motor delivers 2.14 HP (1596 W) to the mill. Thus over the 5-minute period the mill requires 5.18% (1.596 kW×0.0833 h)/0.5 kg=0.266 kW-h/kg) of the energy content of the biomass.

Mechanical disruption of biomass increases the percent of cellulose in the biomass that is in an amorphous, as opposed to a crystalline state. It is shown herein that as milling time is increased, the percent of amorphous component in biomass samples is increased, and the sugar yield from saccharification is also increased. In the present method, the percentage of amorphous cellulose component in the biomass is increased using less energy than would be required if no anhydrous ammonia treatment were included.

In the present method, lignocellulosic biomass is contacted with anhydrous ammonia. Anhydrous ammonia refers to ammonia gas that is dry and not in an aqueous medium. Anhydrous ammonia can be added to a concentration that is between about 2 and about 30 weight percent relative to dry weight of biomass. In one embodiment the anhydrous ammonia is typically between about 10 and about 25 weight percent relative to dry weight of biomass. The biomass and anhydrous ammonia may be maintained at a temperature that is between about 0° C. and about 200° C. A temperature that is between room temperature and about 160° C. may be desired since this requires less energy input to the pretreatment process. The period of time for anhydrous ammonia treatment may be between about thirty minutes to about ten days or longer and up to 1 year if applied in storage. Use of a lower temperature may be combined with a longer treatment time. Also lower anhydrous ammonia concentration may be used at higher temperature. For example, biomass treatment with 20% ammonia at room temperature for nine days or with 10% ammonia at 160° C. for one hour gave approximately the same high sugar yields in saccharification as demonstrated in Example 3 herein. Xylose yield was slightly better with the 160° C. anhydrous ammonia treatment. One skilled in the art will be able to readily determine the combination of parameters within these ranges that gives the desired results using the present method in the particular system employed.

In another embodiment contacting biomass with anhydrous ammonia may be used while maintaining biomass in storage for long periods of time, such as up to a year. While biomass may typically be harvested in the fall, it may be stored and portions used over a period of time until the following harvest. Maintaining the stored biomass in contact with anhydrous ammonia can both treat the biomass to reduce milling time requirement, as described above, as well as act to preserve the biomass while in storage. In this embodiment, typically treatment with anhydrous ammonia would be at natural temperature, that is with no input of energy to either raise of lower the temperature. In addition, the concentration of anhydrous ammonia would typically be in the low range described above, such as between about 2 wt % and 10 wt % relative to dry weight of biomass.

With application of anhydrous ammonia, it is preferred that the moisture content be in a range that supports the benefit of the anhydrous ammonia treatment while readily allowing lowering of the moisture content for the mechanical disruption. In one embodiment the moisture content of the biomass is between about 15% and about 30%, or between about 18% and about 28%, to maximize the benefit of the anhydrous ammonia pretreatment and to allow a lowering of the moisture content to about 15% or less than 15% upon flashing off of the ammonia following ammonia pretreatment. If the biomass is too dry prior to anhydrous ammonia treatment then the efficacy of the ammonia pretreatment may be diminished. The anhydrous ammonia treatment itself will contribute to drying the biomass. During long term storage of biomass, low moisture content reduces biodegradation. To further reduce moisture in the biomass prior to mechanical disruption, the anhydrous ammonia may be heated prior to contacting the biomass, or the anhydrous ammonia may be accompanied by superheated steam, both of which can dry the biomass.

Preferably, the biomass is substantially dry prior to application of mechanical energy for fine milling the biomass. A substantially dry biomass has a moisture content that is equal to or less than about 15%. A moisture content of between about 7% and about 10% was found to be optimal for grinding in a vibratory special-rod mill (Kabeya et al. (1993) Shikoku Kogyo Gijutsu Shikensho Kenkyu Hokoku 24:42-90) and is desired in the present process. As drying contributes significantly to the cost of the process, an advantage to using anhydrous ammonia treatment is in reduction or elimination of the need for further drying following the anhydrous ammonia treatment.

However, if following anhydrous ammonia treatment, further drying is desired, the biomass may be dried to reach a dry matter content of at least about 80%. Preferably the dry matter content is at least about 85%, 90%, 93%, 96%, or higher during application of mechanical energy as described below. Drying may be by any conventional means such as using a drying oven, rotary dryer, flash dryer, or superheated steam dryer, or air drying.

In the present method, mechanical energy is applied to anhydrous ammonia-treated biomass, or during anhydrous ammonia treatment of biomass, to produce fine-milled, anhydrous ammonia treated biomass. Fine-milled material may be produced by milling that applies forces such as pounding, crushing, shearing, or grinding to biomass. Typically a combination of more than one of these types of forces is applied in a milling treatment such as pounding, crushing, shearing and grinding in a ball mill or attritor mill. Any means of mechanically disrupting biomass may be used in the present invention including, but not limited, to attritor milling, hammer milling, ball milling, bead milling, vibratory ball milling, vibratory rod milling, jet milling, pin milling, turbine milling, air classifier milling, roll milling and planetary ball milling. When used for fine milling, hammer milling is a component of an air classifier mill where larger particles are recycled through the hammer mill repeatedly until they are small enough to exit the mill at a specified size.

In conventional ball milling, a large rotating cylinder contains dense spherical balls (also called beads) inside that grind material by impacting it with force (or pounding) as the cylinder rotates. In attritor milling, spherical beads (also called balls) inside a stationary cylinder are stirred by a spinning shaft on which are affixed perpendicularly oriented arms. Beads, or balls, for milling may be any type of dense spherical bead such as cubic Zirconia beads or stainless steel beads. The size of bead used may vary depending on conditions such as the particular apparatus in which they are used and specific biomass to be processed, including type of biomass and initial particle size, as well as the specific anhydrous ammonia treatment applied to the biomass. Balls may be, for example, 0.3175 cm, 0.471 cm, 0.556 cm, 0.635 cm, 0.794 cm, 0.953 cm, or larger. Balls or beads that are greater than 0.3175 cm in diameter may provide more effective milling. The most effective ball size for a particular biomass and set of treatment parameters may be readily determined by one skilled in the art.

With prior or concurrent anhydrous ammonia treatment, mechanical disruption may occur over a period of time that is between about several seconds to about several days. For example, disruption may run for less than about two days, or a time that is less than about one day. In addition, times of about 60, 50, 40, 30, 20, 10, 5, or 1 minutes or less may be used. Short application times may be used to reduce energy costs, though maximal sugars yields may not be achieved during saccharification. For example, a 5 or 10 minute milling time can produce a level of sugars that may be commercially acceptable, but are not as high as achieved with longer milling times. The balance of energy costs of milling and sugars yields may be adjusted to support maximal commercial value.

Mechanical disruption means may be applied in a batch process, or in a continuous process.

Pretreated Biomass Product

The pretreated biomass product resulting from the present process is readily saccharifiable and is saccharified to produce fermentable sugars that may be used by a biocatalyst in fermentation to produce a desired target product. Enzymatic saccharification typically makes use of an enzyme consortium for breaking down cellulose and hemicellulose to produce a hydrolysate containing sugars including glucose, xylose, and arabinose. Saccharification enzymes are reviewed in Lynd, L. R., et al. (Microbiol. Mol. Biol. Rev., 66:506-577, 2002).

At least one enzyme is used, and typically a saccharification enzyme consortium is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme.

Saccharification enzymes may be obtained commercially, such as Spezyme® CP cellulase, Multifect® xylanase, Accelerase® 1500, and Accellerase® DUET (Danisco U.S. Inc., Genencor International, Rochester, N.Y.). In addition, saccharification enzymes may be unpurified and provided as a type of cell extract or whole cell lysate. The enzymes may be produced using recombinant microorganisms that have been engineered to express multiple saccharifying enzymes.

Of particular value in the present invention are classes of glycoside hydrolases, such as the families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and are available in the Carbohydrate-Active enzyme (CAZy) database (Cantarel et al. (2009) Nucleic Acids Res. 37 (Database issue):D233-238). These enzymes are able to act on a number of substrates and are effective in the saccharification process. Glycoside hydrolase family 3 ("GH3") enzymes have a number of known activities: β-glucosidase (EC:3.2.1.21); β-xylosidase (EC: 3.2.1.37); N-acetyl β-glucosaminidase (EC:3.2.1.52); glucan β-1,3-glucosidase (EC:3.2.1.58); cellodextrinase (EC: 3.2.1.74); exo-1,3-1,4-glucanase (EC:3.2.1); and β-galactosidase (EC 3.2.1.23). Glycoside hydrolase family 39 ("GH39") enzymes have α-L-iduronidase (EC:3.2.1.76) or β-xylosidase (EC:3.2.1.37) activity. Glycoside hydrolase family 43 ("GH43") enzymes have the following activities: L-α-arabinofuranosidase (EC 3.2.1.55); β-xylosidase (EC 3.2.1.37); endoarabinanase (EC 3.2.1.99); and galactan 1,3-β-galactosidase (EC 3.2.1.145). Glycoside hydrolase family 51 ("GH51") enzymes have L-α-arabinofuranosidase (EC 3.2.1.55) or endoglucanase (EC 3.2.1.4) activity. Glycoside hydrolase family 10 ("GH10") are more fully described in Schmidt et al., 1999, Biochemistry 38:2403-2412 and Lo Leggio et al., 2001, FEBS Lett 509: 303-308) and the Glycoside hydrolase family 11 ("GH11") are more fully described in Hakouvainen et al., 1996, Biochemistry 35:9617-24.

Prior to fermentation the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the biocatalyst(s) used during fermentation and the pH used during saccharification, the pH may be adjusted to that suitable for fermentation.

The saccharification can be performed for a time of about several minutes to about 200 hours, typically from about 24 hours to about 72 hours. The time for the reaction will depend on the enzyme concentration and the specific activity, as well as the substrate used and the environmental conditions, such as temperature and pH. One skilled in the art can readily determine optimal conditions of temperature, pH and time to be used with a particular substrate and saccharification enzyme consortium.

The saccharification can be performed in a single batch, fed-batch or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The percent of solids in a saccharification process may vary. It is desirable to keep the percent of solids used in saccharification relatively high in order to obtain a hydrolysate with a high concentration of fermentable sugars. Typically solids are between about 10% and 60%, with solids between about 10% and 25% more typical.

The degree of solubilization of sugars from biomass following saccharification can be monitored by measuring the release of monosaccharides and oligosaccharides. Methods to measure monosaccharides and oligosaccharides are well known in the art. In addition to monomer sugars, soluble oligomeric sugars are produced which may be converted to monomers for use by biocatalysts in fermentation.

Biomass hydrolysate containing fermentable sugars are included in fermentation medium typically as a percent of the medium, providing all or a portion of the carbon source for biocatalyst growth and product production. The hydrolysate in a fermentation medium is typically about 40% to 90% of the fermentation medium. Examples of hydrolysate used as 40% or 80% of fermentation medium are given in Example 9 of US 20070031918 A1, incorporated herein by reference. Depending on the fermentable sugars concentration in the hydrolysate, additional sugars may be added to the medium. For example, when a hydrolysate containing about 80 g/L glucose and about 50 g/L xylose is included at 40% of the fermentation medium, additional glucose and xylose may be added to the desired final sugars concentrations. In addition to hydrolysate, fermentation medium may contain other nutrients, salts and factors required for growth and production by the specific biocatalyst to be used for product production, as well known to one skilled in the art. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction.

Alternatively to preparing hydrolysate, adding it to fermentation medium, then carrying out the fermentation, a simultaneous saccharification and fermentation (SSF) process may be used to produce a biomass hydrolysate fermentation broth. In this process sugars are produced from biomass as they are metabolized by the production biocatalyst.

Biocatalyst Fermentation and Target Products

Fermentable sugars in the fermentation medium are metabolized by suitable biocatalysts to produce target products. The sugars are contacted with a biocatalyst in a fermentation process where the biocatalyst is grown under conditions where a target product made by the biocatalyst is produced. Temperature and/or headspace gas may be adjusted for fermentation, depending on conditions useful for the particular biocatalyst(s) in use. Fermentation may be aerobic or anaerobic. These and other conditions including temperature and pH are adjusted for the particular biocatalyst used.

Examples of target products produced by biocatalysts include 1, 3-propanediol, butanol (isobutanol, 2-butanol, and 1-butanol), and ethanol. Disclosed in U.S. Pat. No. 7,504,250 are recombinant microorganisms that produce 1,3-propanediol. Production of butanol by genetically modified yeast is disclosed for example in US 20070092957 A1. Genetically modified strains of E. coli have also been used as biocatalysts for ethanol production (Underwood et al., (2002) Appl. Environ. Microbiol. 68:6263-6272). Ethanol has been produced by genetically modified Zymomonas in lignocellulosic biomass hydrolysate fermentation media (US 20070031918 A1). Genetically modified strains of Zymomonas mobilis with improved production of ethanol are described in US 2003/0162271 A1 and US 2009/0246846 A1.

EXAMPLES

The following abbreviations are used:
"HPLC" is High Performance Liquid Chromatography, "C" is Celsius, "m" is meter, "mm" is millimeter, "µm" is micrometer, "µL" is microliter, "mL" is milliliter, "L" is liter, "N" is normal, "min" is minute, "mM" is millimolar, "cm" is centimeter, "g" is gram, "mg" is milligram, "kg" is kilogram, "wt" is weight, "h" or "hr" is hour, "d" is day, "RT" is room temperature, "DM" is dry matter, "DWB" is dry weight of biomass, "ASME" is the American Society of Mechanical Engineers, "s.s." is stainless steel, "in" or """ is inch, "rpm" is rotations per minute, "OD" is optical density, "r" is radius, "$d_{50}$" is median particle size in a sample.

General Methods
Biomass Characterization

Dry matter content of biomass was determined using a Denver Instruments IR-120 moisture analyzer operating at 105° C., or by heating in a vacuum oven overnight at 102° C. with a nitrogen bleed (equivalent to ~12 inches of mercury).

The composition of biomass is measured by any one of the standard methods well known in the art, such as ASTM E1758-01 "Standard method for the determination of carbohydrates by HPLC".

Ammonia Treatment System (P5L reactor)

Ammonia treatment experiments were performed using a system that consisted of a 5 L horizontal cylindrical pressure vessel (Littleford Day, Florence, Ky.) modified to include a 1.5" (3.8 cm) ball valve on the top of the reactor, which could be removed to charge biomass. The reactor was equipped with two ports in the headspace, a 1.5" ball valve on the bottom, various thermocouples, a relief valve, a pressure gage, and a pressure transducer. The reactor contained a so-called "heat transfer" type impeller, which contained four blades for mixing solids vertically and horizontally. The impeller was rotated at approximately 40 rpm for all experiments.

Anhydrous ammonia was metered into the P5L reactor by placing an 2 lb cylinder of anhydrous ammonia on an electronic balance, and then measuring the weight loss of the cylinder to obtain the target amount of ammonia per dry matter in the reactor.

A needle valve connected to the top flange was used to control the pressure flash and vacuum flash. The flash vapors were passed through a tube-in-tube heat exchanger which used house cold water. The vapors/condensate was then collected in a 2 L cylindrical vessel which was jacketed with wet ice. The 2 L cylinder was evacuated of non-condensables prior to the pressure flash. The vacuum was then broken, and the condensate collected. The same system was then used to collect the vacuum flash condensate.

Enzyme Sources

Spezyme® CP, Multifect® xylanase, and Accellerase® 1500 were from Danisco U.S. Inc., Genencor, International (Rochester, N.Y.). Novozyme 188 was from Novozymes (2880 Bagsvaerd, Denmark).

Example 1 (Comparative)

Ball-Milling of Cob or Switchgrass Biomass as a Sole Pretreatment

Figure 1B:
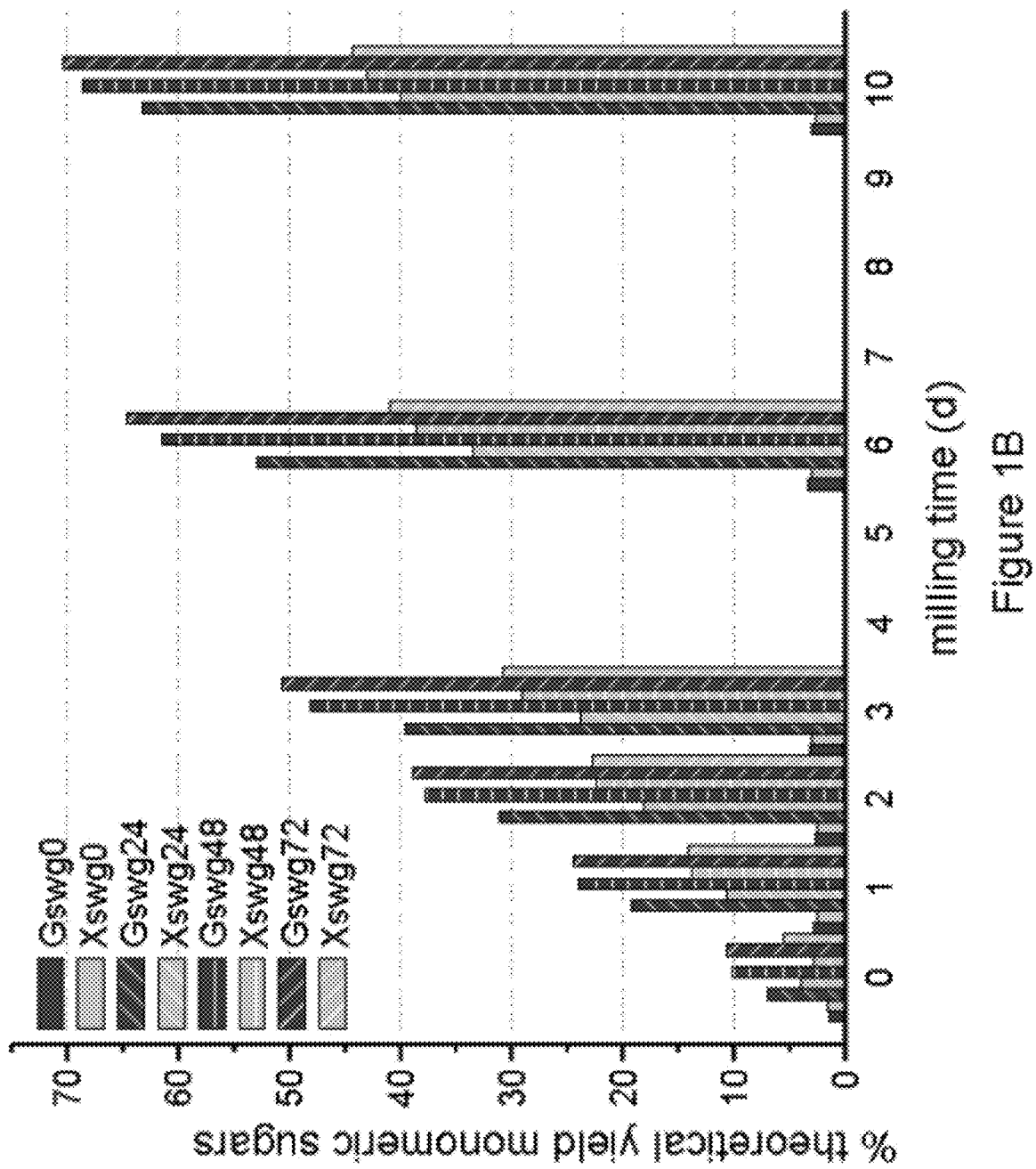

Ball-milling was examined as a non-chemical means to prepare cob and late winter/early spring-harvested switchgrass lignocellulosic biomass for saccharification. Five grams of knife-milled (passed through a 1 mm sieve) cob (94% DM) and switchgrass (94% DM) were each placed in 125 mL plastic bottles with 226 g of 1 cm size $Y_2O_3$-doped $ZrO_2$ beads (cubic Zirconia beads; Norstone; Wyncote, Pa.). The bottles were tumbled end over end at a rate of 83 cycles per minute at room temperature for 1-10 d. Aliquots were taken at regular intervals and used for enzymatic saccharification. Approximately 370 µL of suspension of a 14% solids suspension were saccharified in 50 mM NaCltrate containing Spezyme CP:Multifect® xylanase:Novozyme 188 at 6.68: 3.34:1.67 mg/g solids, at pH 4.7-4.8 and 47° C. using a rotary shaker at 250 rpm in 6 mL glass vials containing two 5 mm glass beads. Aliquots were taken at regular intervals and subjected to HPLC analysis using an HPX-87H column (Bio-Rad) run at 60° C. with 0.01 N $H_2SO_4$ as the mobile phase at a flow rate of 0.6 mL/min. Percent of theoretical yields of glucose and xylose in samples saccharified for different times (0, 24, 48, 72 hours), and milled for different times (0, 1, 2, 3, 6, 10 days) are shown in FIG. 1 for cob (A) and switchgrass (B).

Milling using the $Y_2O_3$-doped $ZrO_2$ beads had a major impact on the saccharification of these feedstocks, with no additional chemical pretreatment or lignin removal. For both cob and switchgrass, increased milling times produced increased yields of glucose and xylose. Yields were lower for switchgrass than for cob through 3 days of milling. After 6 days of milling, with 72 h saccharification, for both cob and switchgrass yields reached about 65% for glucose and about 40% for xylose. At 10 days of milling, cob yields increased slightly and switchgrass yields increased to about 70% glucose and about 45% xylose.

Example 2 (Comparative)

Saccharification Yields Correlate with Amorphous Structure of Switchgrass Biomass Following Ball Milling Stainless steel has a higher density than $ZrO_2$ (7.7 g/cm$^3$ and 6.0 g/cm$^3$, respectively) and stainless steel beads were used as an alternative milling material.

Five grams of knife milled (passed through a 1 mm sieve) late winter/early spring-harvested switchgrass (91.3% DM) were placed in 125 mL plastic bottles with 200 g of stainless steel ¼" (0.63 cm) beads. The bottles were tumbled end over end at a rate of 83 cycles per minute at room temperature for 1-10 d of milling. Aliquots were taken at regular intervals and used for enzymatic saccharification, particle size determination, surface area measurements and wide-angle X-ray diffraction for crystallinity. The enzymatic saccharifications were performed in 50 mM NaCltrate, pH 4.9 at a solids loading of 14% using Accelerase® 1500 (Genencor) 25 mg/g glucan, and a cocktail of hemicellulases (Xyn3, Fv3A, Fv51A, and Fv43D) at 16.6 mg/g xylan. Approximately 370 µL of suspension were saccharified at 47° C. using a rotary shaker at 250 rpm in 6 mL glass vials containing two 5 mm glass beads. Aliquots were taken at regular intervals and subjected to HPLC analysis as in Example 1.

Figure 2A:
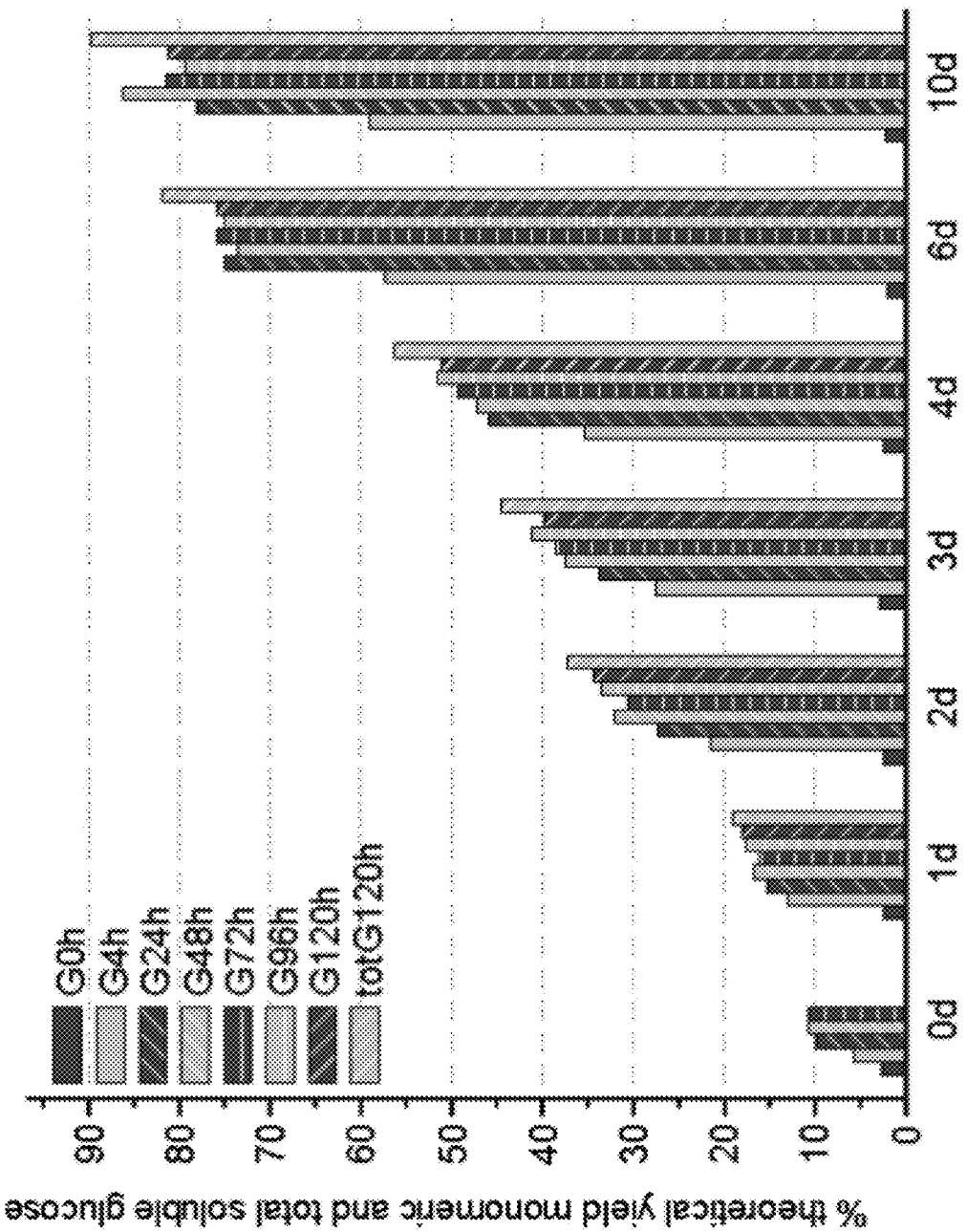
FIG. 2 shows graphs of percent of theoretical yields of glucose (G) in (A) and xylose (X) in (B) in 1 mm knife milled untreated late winter/early spring harvested switchgrass samples saccharified (14% solids loading) for different times (0, 24, 48, 72, 96, 120 hours), plotted against time the biomass was milled with 0.25" (0.635 cm) stainless steel beads (0, 1, 2, 3, 6, 10 days) at a ratio of 200 g of beads to 5 g biomass. All bars are monomeric sugars except for the last bar of each set which is the total soluble sugar yield (monomer and oligomer) for glucose in (A) and xylose in (B).
Figure 2B:
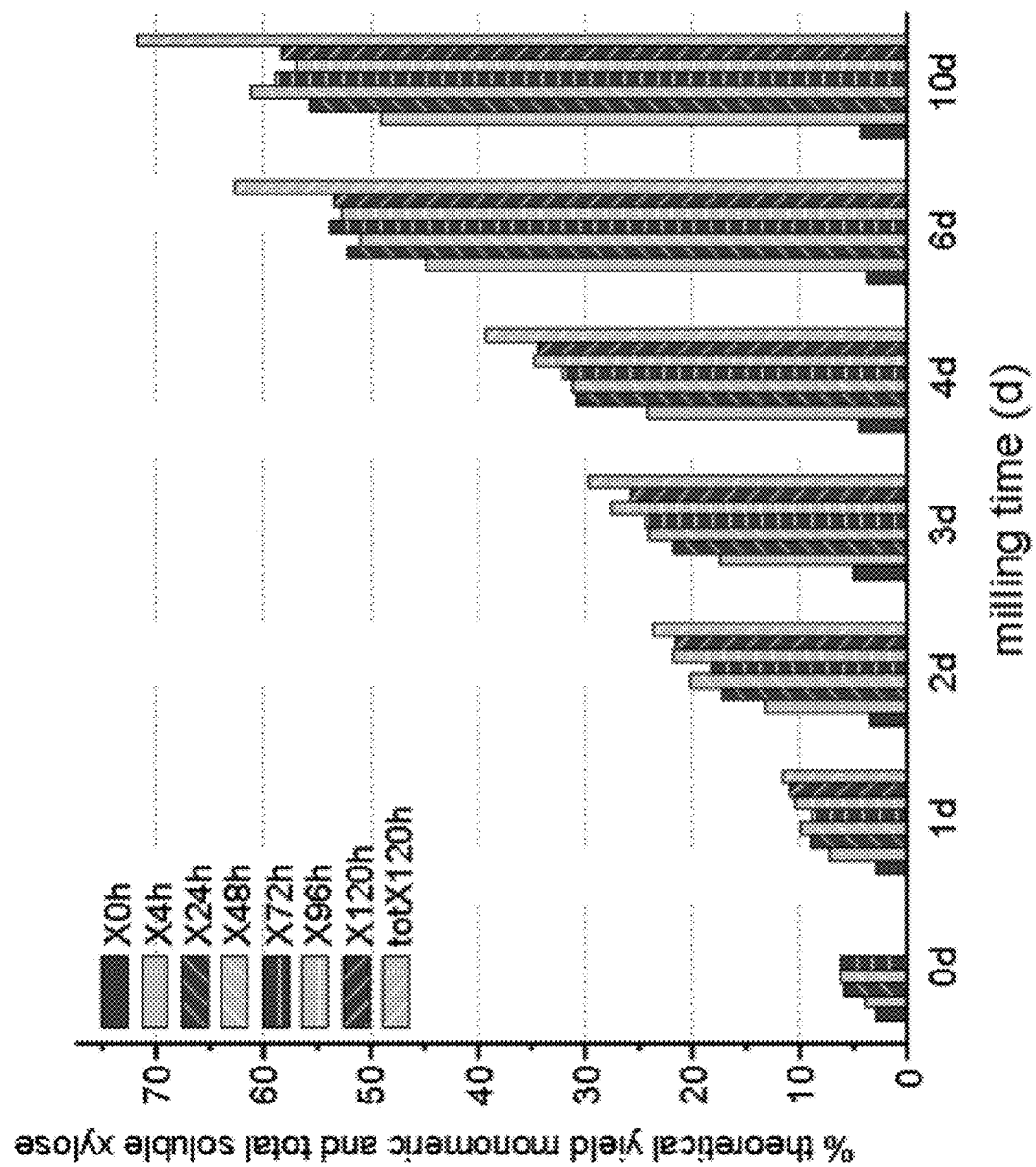

FIG. 2 shows the monomeric glucose and xylose yields (FIGS. 2A and B, respectively) obtained at various milling and saccharification times. Also shown for each milling time is the total solubilized sugar (monomeric plus oligomeric glucose and xylose) determined by filtration, after 120 h of saccharification, to remove insoluble biomass followed by heating at 121° C. for 1 h in the presence of 4% $H_2SO_4$ and HPLC sugar analyses.

Figure 3A:
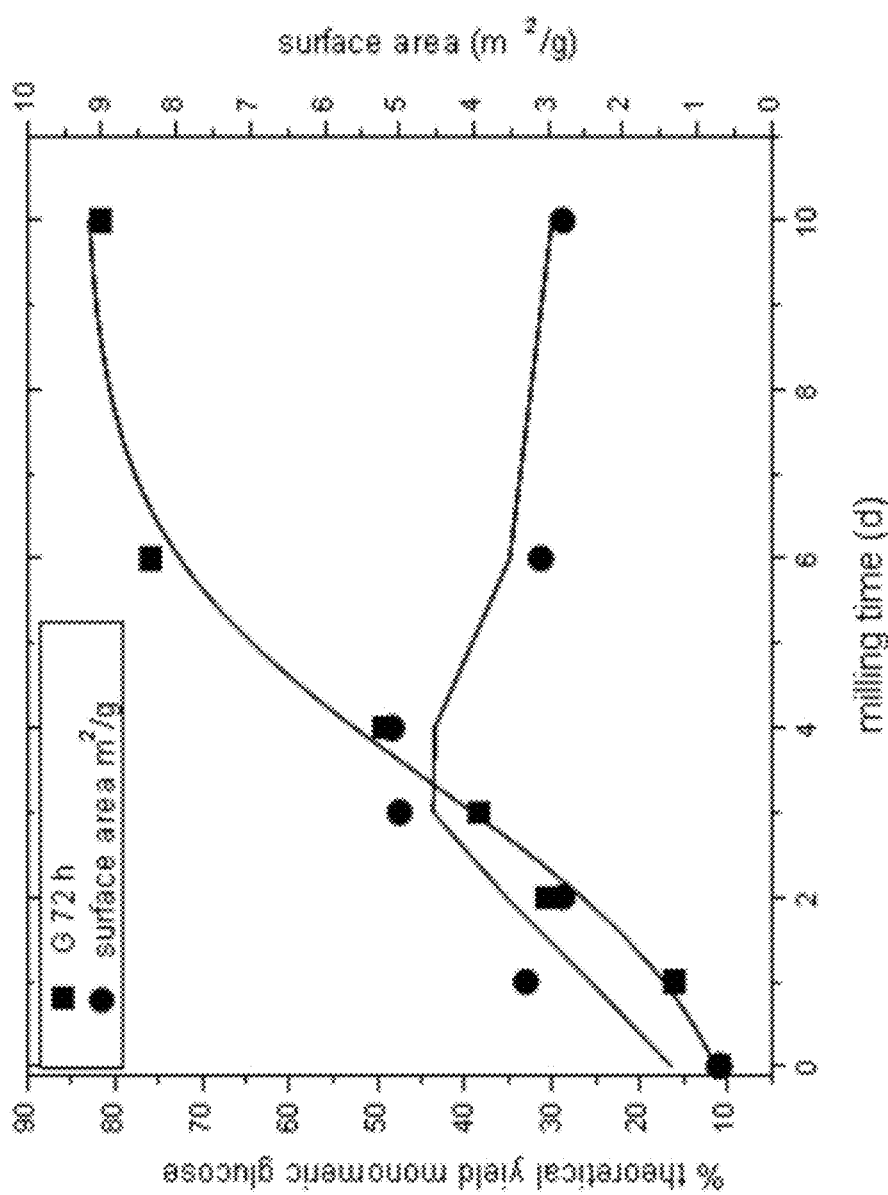
FIG. 3 shows graphs of percent of theoretical yields of monomeric glucose (A) and xylose (B) at 72 hours of saccharification (at 14% solids loading) of the switchgrass of FIG. 2 compared to particle surface area ($m^2$/g) of biomass, both as a function of milling time.
Figure 3B:
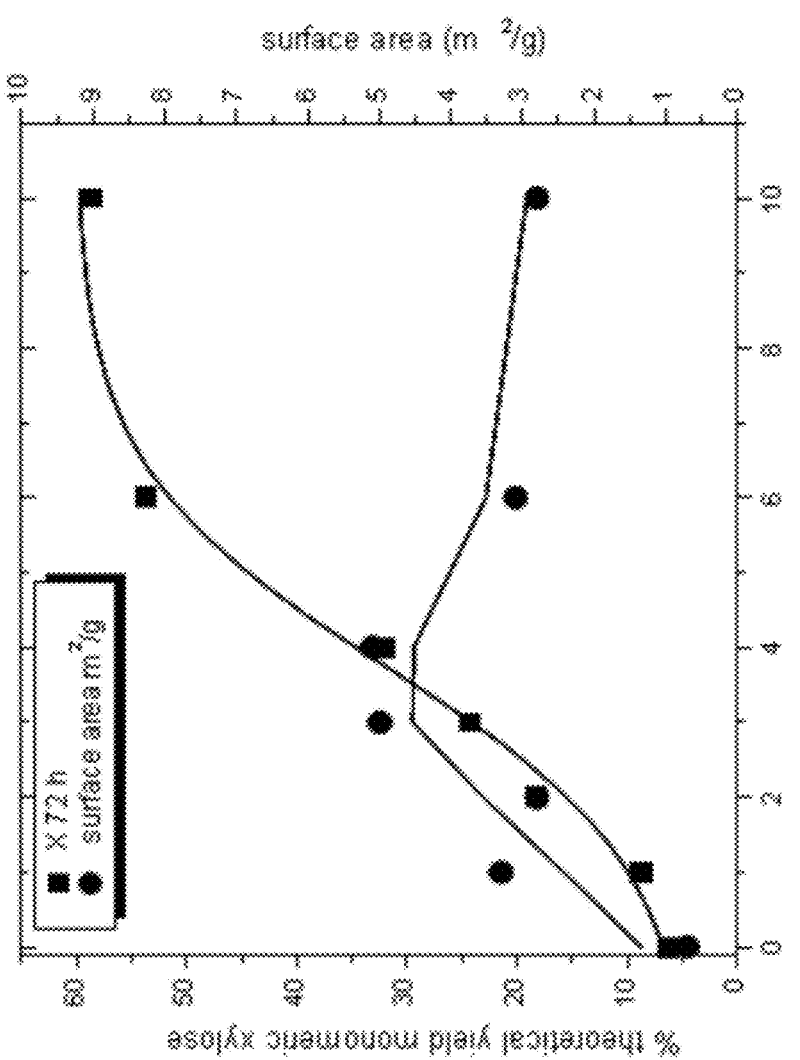
Figure 4A:
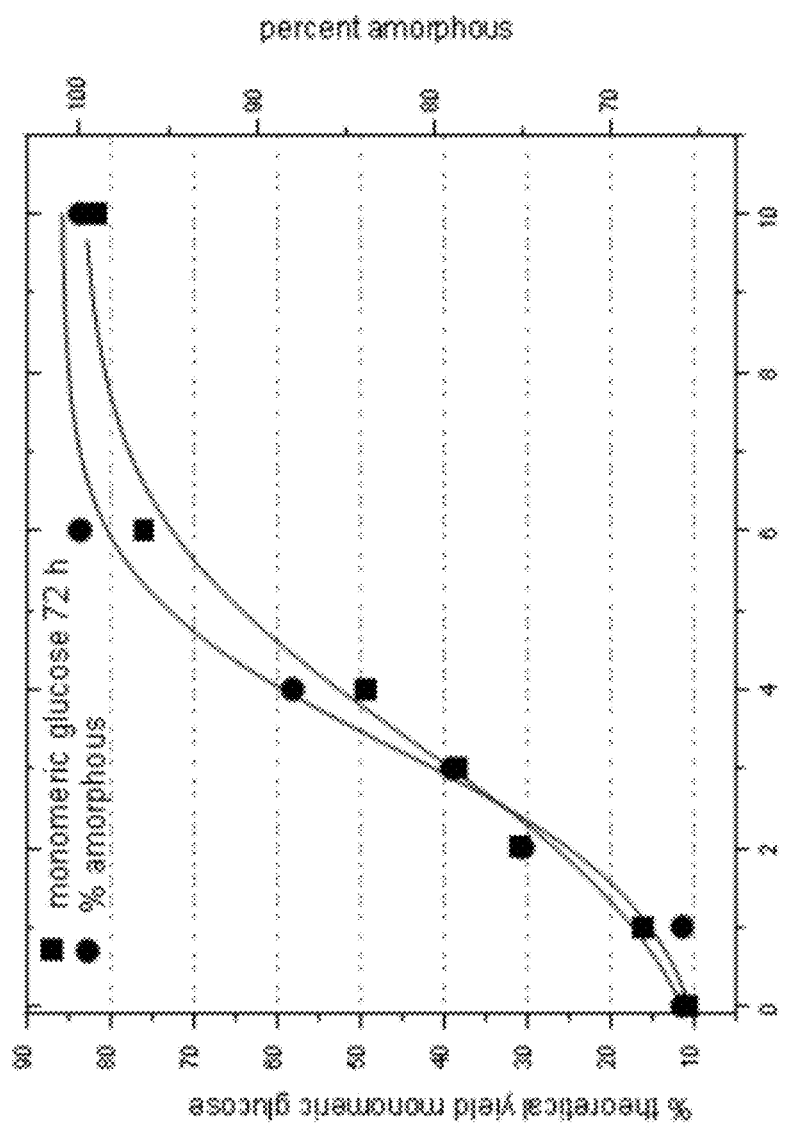
FIG. 4 shows graphs of percent of theoretical yields of monomeric glucose (A) and xylose (B) at 72 hours of saccharification (at 14% solids loading) of the switchgrass of FIG. 2 compared to percent amorphous component of biomass, both as a function of milling time.
Figure 4B:
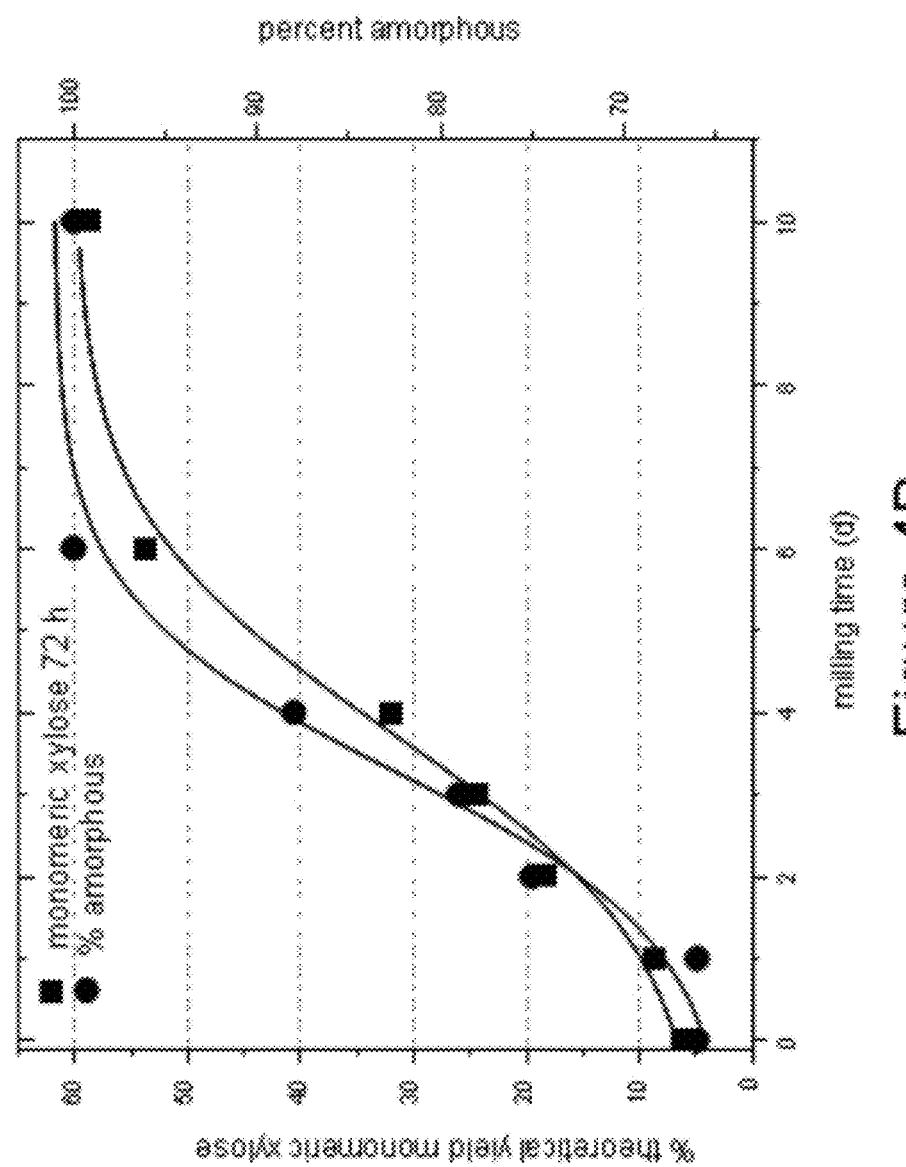

The glucose and xylose yields increased with increased milling time, showing sigmoidal kinetics over the first six days of milling for both sugars (FIGS. 3A and B, respectively). The sigmoidal shape likely reflects a lowering of the energy required for incremental fracture of the biomass as the biomass was increasingly fragmented. The surface area of the particles (FIGS. 3A and B) was measured using $N_2$ gas adsorption. The surface area increased from 0 to 3-4 d of milling after which it decreased, which could be due to the collapse of some structural element with further milling. The saccharification yield surprisingly did not track the particle surface area except at the early stages of milling, indicating that there are factors in addition to surface area that determine the rate and yield of saccharification. Another contributing factor may be a decrease in cellulose crystallinity. The crystallinity of the biomass was assessed using wide angle x-ray scatter as a function of milling time and plotted with glucose and xylose yields (FIGS. 4A and B, respectively). The crystallinity data is also shown in numeric form in Table 2. The saccharification yields tracked closely the percent amorphous component in the biomass, indicating that the crystallinity or a factor related to the crystallinity (e.g. degree of polymerization) contributes to the increased accessibility of the polysaccharide to the saccharifying enzymes.

A comparison of FIGS. 1 and 2 indicates that after 10 d of ball milling the saccharification yields were higher with the ¼" stainless steel beads than with the 1 cm $Y_2O_3$ doped $ZrO_2$ beads.

Steel ball-milling of switchgrass greatly accelerated enzymatic saccharification (≥50% of final sugar yield released in 4 h), producing a final yield of monomeric sugars of >80% for glucose and ~60% for xylose after 10 d of milling.

TABLE 2

Percent crystallinity as a function of milling time for switchgrass determined using wide-angle x-ray scatter.

| Sample | % amorphous | % crystalline |
|---|---|---|
| Switchgrass unmilled | 66 | 34 |
| Switchgrass milled 1 d | 66 | 34 |
| Switchgrass milled 2 d | 75 | 25 |
| Switchgrass milled 3 d | 79 | 21 |
| Switchgrass milled 4 d | 88 | 12 |
| Switchgrass milled 6 d | 100 | 0 |
| Switchgrass milled 10 d | 100 | 0 |

Example 3

Effects of Treatment with Anhydrous Ammonia and Ball Milling

Fall-harvested switchgrass (92.5% DM) was either untreated (UT4un) or treated with anhydrous ammonia at 20% by dry wt. of biomass at room temperature (RT) for 9 d or at 10% by dry wt. of biomass at 160° C. for 1 h (JV198). For the 160° C. treatment, the switchgrass was placed in the P5L reactor described in General Methods and the jacket of the reactor was heated. Ammonia was added from a cylinder of anhydrous ammonia.

The RT treated biomass was knife-milled through a 1 mm screen following the ammonia treatment, while the 160° C. treated biomass was knife-milled through a 1 mm screen prior to ammonia treatment. The ammonia was flashed off and the samples were then milled for 0, 19, 43 and 67 h using ¼ inch (0.635 cm) stainless steel beads as described in Example 2. The biomass was then saccharified using the same conditions in Example 2. Sugar yields were assayed as in Example 1.

Figure 5A:
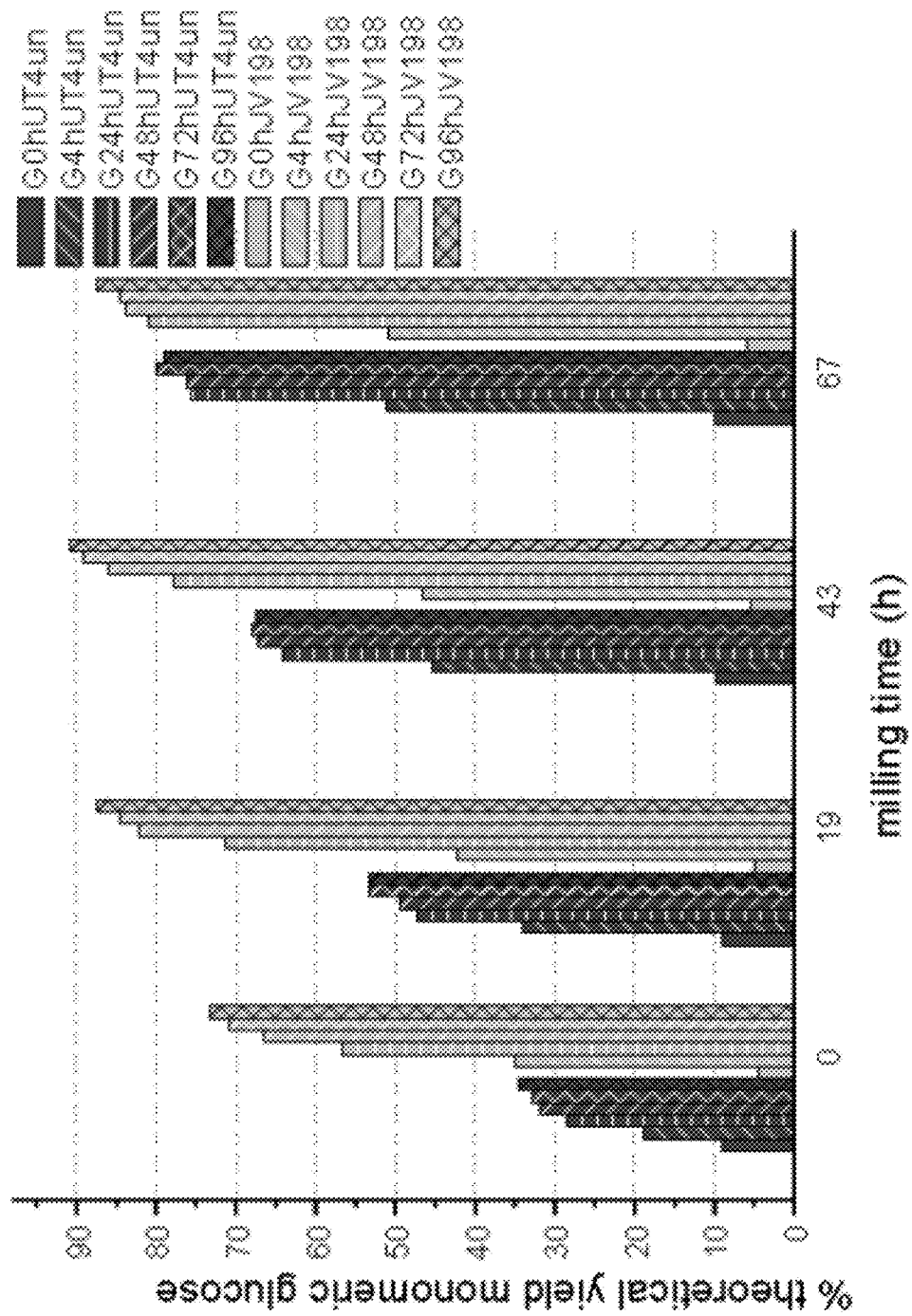
FIG. 5 shows graphs of percent of theoretical saccharification yields of monomeric glucose (A) and xylose (B) of 1 mm knife milled untreated fall-harvested switchgrass (UT4) and 1 mm knife-milled fall-harvested switchgrass treated with 10 wt % anhydrous ammonia at 160° C. for 1 hour (JV198). The samples were milled as in FIG. 2 for different times (0, 19, 43, 67 hours) after which they were saccharified for 0, 4, 24, 48, 72, or 96 hours (at 14% solids loading).
Figure 5B:
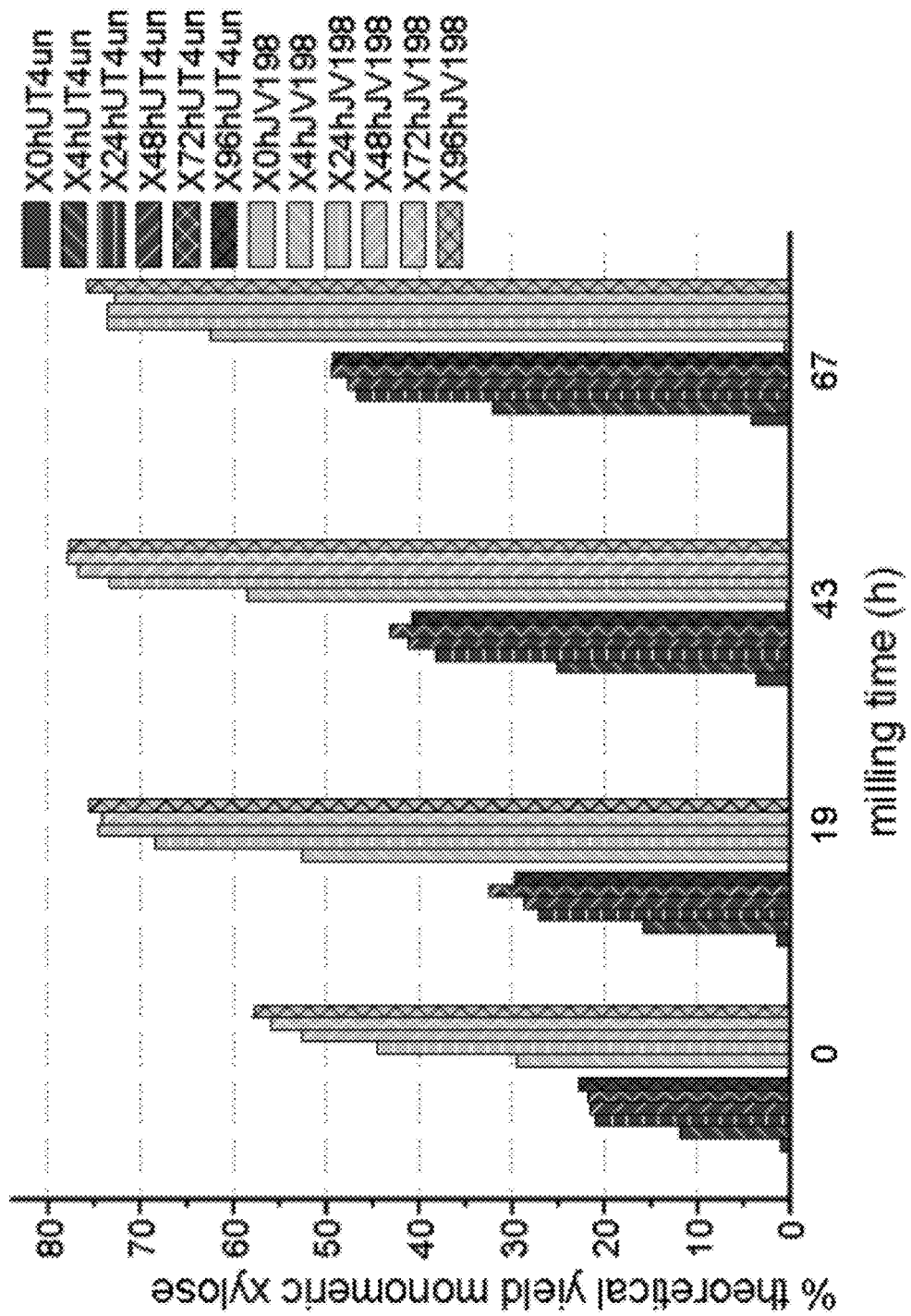

Glucose and xylose yields following different times of saccharification for samples treated with anhydrous ammonia at 10% by wt. biomass at 160° C. for 1 h (JV198) with different ball milling times are shown in FIGS. 5 A and B. respectively. Also shown are yields for untreated controls (UT4un) that were ball milled but not treated with anhydrous ammonia. Results show that higher yields of glucose and of xylose were achieved with the combination of anhydrous ammonia and ball milling than with milling alone for each ball milling time point. The increase in saccharification yield was particularly high for xylose, which increased by over a factor of 2 for the 19 h milled sample.

Samples treated with 20% anhydrous ammonia by wt. of biomass at RT for 9 d gave similar results. Results from both anhydrous ammonia treatments and the ball milled only (untreated) controls with saccharification for 72 h are shown as exponential plots of the percent of theoretical monomeric saccharification yields versus ball milling time in FIG. 6. Table 3 gives calculations of the rise times derived from the exponential fits of the curves of FIG. 6. The rise curves were fit with a single exponential. The rise time (tau) is the time it takes to go to the 1/e value of the exponential rise (where e=2.7183, 63% of the relaxation). The results show that for both ammonia pretreatments, the rates of increase in saccharification yields with milling time were 6-10 times faster than for the untreated sample.

TABLE 3

Figure 6:
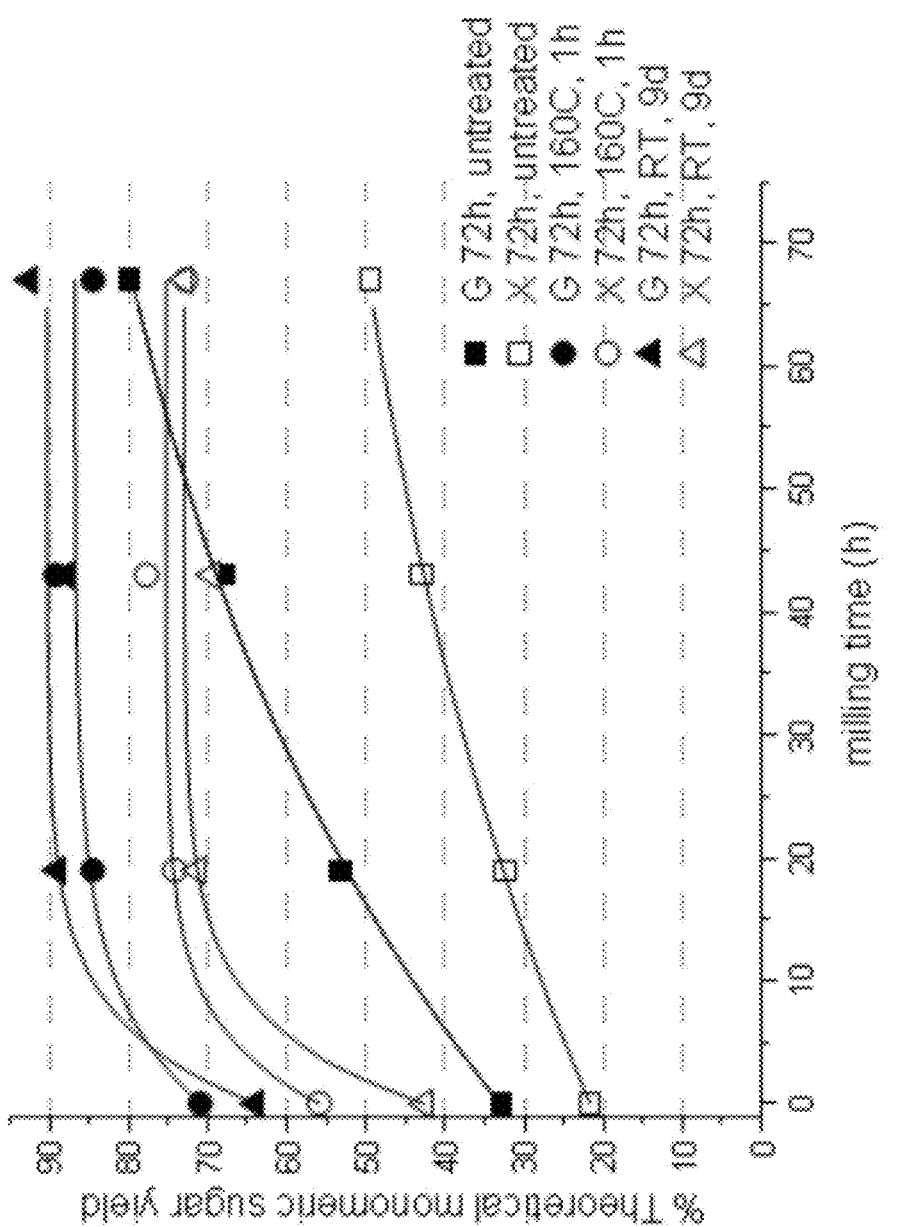
FIG. 6 shows a graph of percent of theoretical saccharification yields of monomeric glucose (G) and xylose (X) of 1) 1 mm knife milled untreated fall-harvested switchgrass, 2) 1 mm knife milled fall-harvested switchgrass treated with 10 wt % anhydrous ammonia and 3) coarse milled fall-harvested switchgrass treated for 9 days with 20 wt % anhydrous ammonia and then 1 mm knife milled. The samples were then milled for different times (0, 19, 43, 67 hours) as in FIG. 2, after which they were saccharified for 72 h (at 14% solids loading).

Rise times for xylose or glucose yield plots in FIG. 6

| Anhydrous ammonia treatment | Sugar | Rise time (τ) |
|---|---|---|
| untreated | glucose | 54.4 h |
| untreated | xylose | 65.3 h |
| 10%, 160° C., 1 h | glucose | 8.92 h |
| 10%, 160° C., 1 h | xylose | 6.22 h |
| 20%, RT, 9 d | glucose | 6.54 h |
| 20%, RT, 9 d | xylose | 6.55 h |

Example 4

Figure 7A:
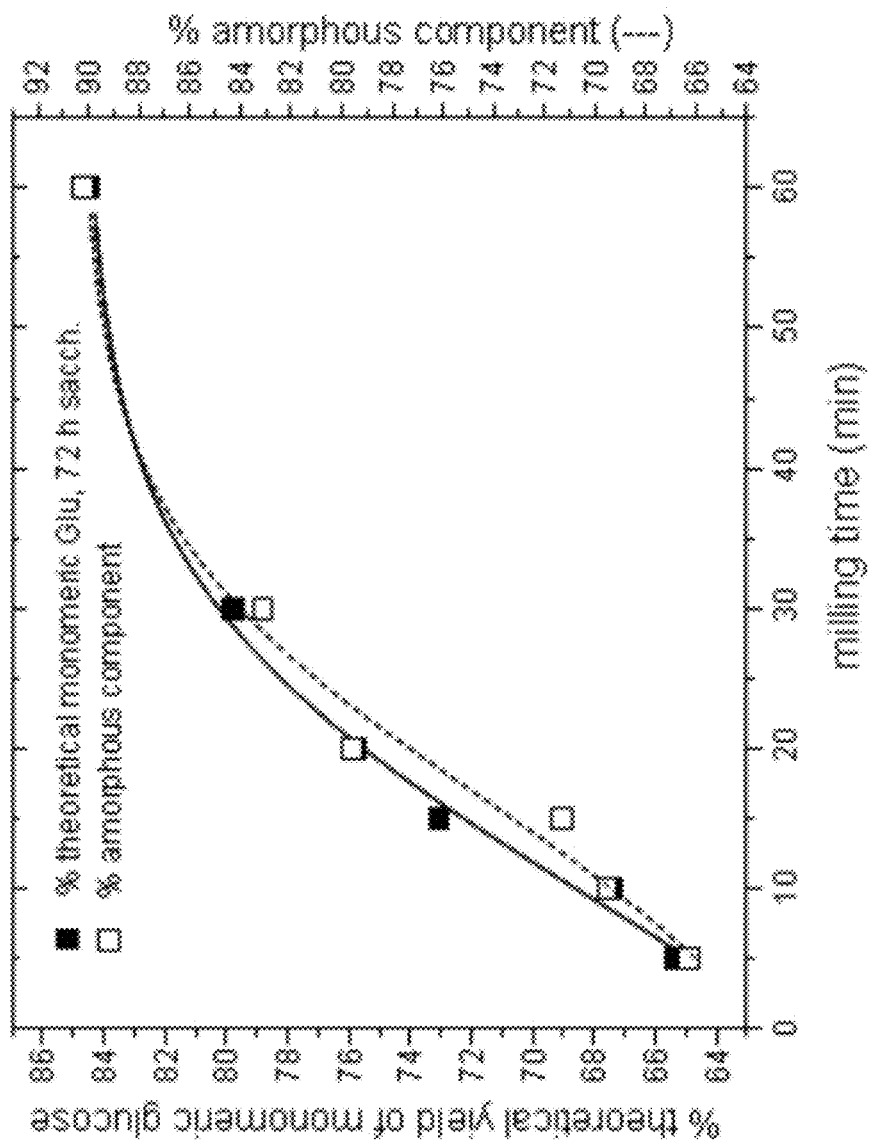
FIG. 7 shows graphs of percent of theoretical saccharification yields of monomeric glucose (A) and xylose (B) of 1 mm knife milled fall-harvested switchgrass treated with 10 wt % anhydrous ammonia at 160° C. for 1 hour, attritor milled for different times (min) with 0.25" (0.635 cm) stainless steel beads (at a ratio of 40 lbs. of beads to 500 g biomass) and saccharified for 72 h (at 14% solids loading); compared to percent amorphous component in the treated samples.
Figure 7B:
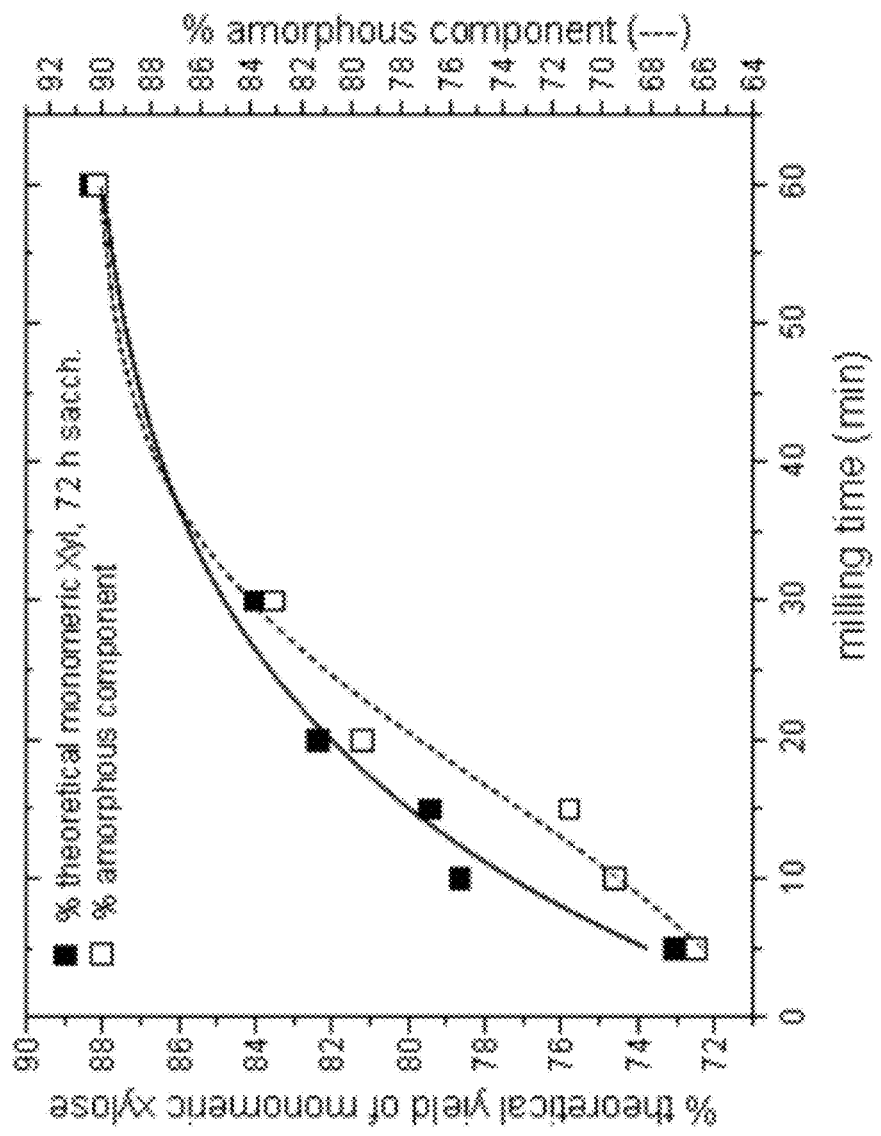

Comparison of Saccharification of Anhydrous Ammonia Treated and Attritor-Milled Switchgrass with Respect to Particle Size and Amorphous Component Five hundred grams of knife-milled (passed through a 1 mm screen) fall-harvested switchgrass was anhydrous ammonia-treated at 160° C. for 1 h as in Example 5. Samples of the switchgrass were then attritor milled at 516 rpm with 40 lbs. of ¼" stainless steel beads for between 0 and 60 min in a Union Process SD-1 attritor mill. Each sample was submitted for crystallinity analysis using wide angle x-ray scatter. Table 4 shows the percent amorphous component derived from the diffraction pattern for each of the samples and the $d_{50}$ particle size in microns. The particle size reached a minimum after 20 min of milling and then increased with increased milling time as was observed earlier for the particle surface area of untreated switchgrass (Example 2), while the % amorphous component continued to increase. Samples were saccharified as in Example 2 and sugar yields assayed as in Example 1. FIGS. 7A and B show a comparison of the percent amorphous component and the percent of theoretical yields upon saccharification for 72 h. The saccharification yields for glucose (FIG. 7A) track fairly closely the percent amorphous component as seen previously for milled switchgrass with no anhydrous ammonia pretreatment (Example 2), showing in both cases a modest sigmoidal shape. The xylose saccharification yields (FIG. 7B) are somewhat more exponential than the percent amorphous component.

Figure 8:
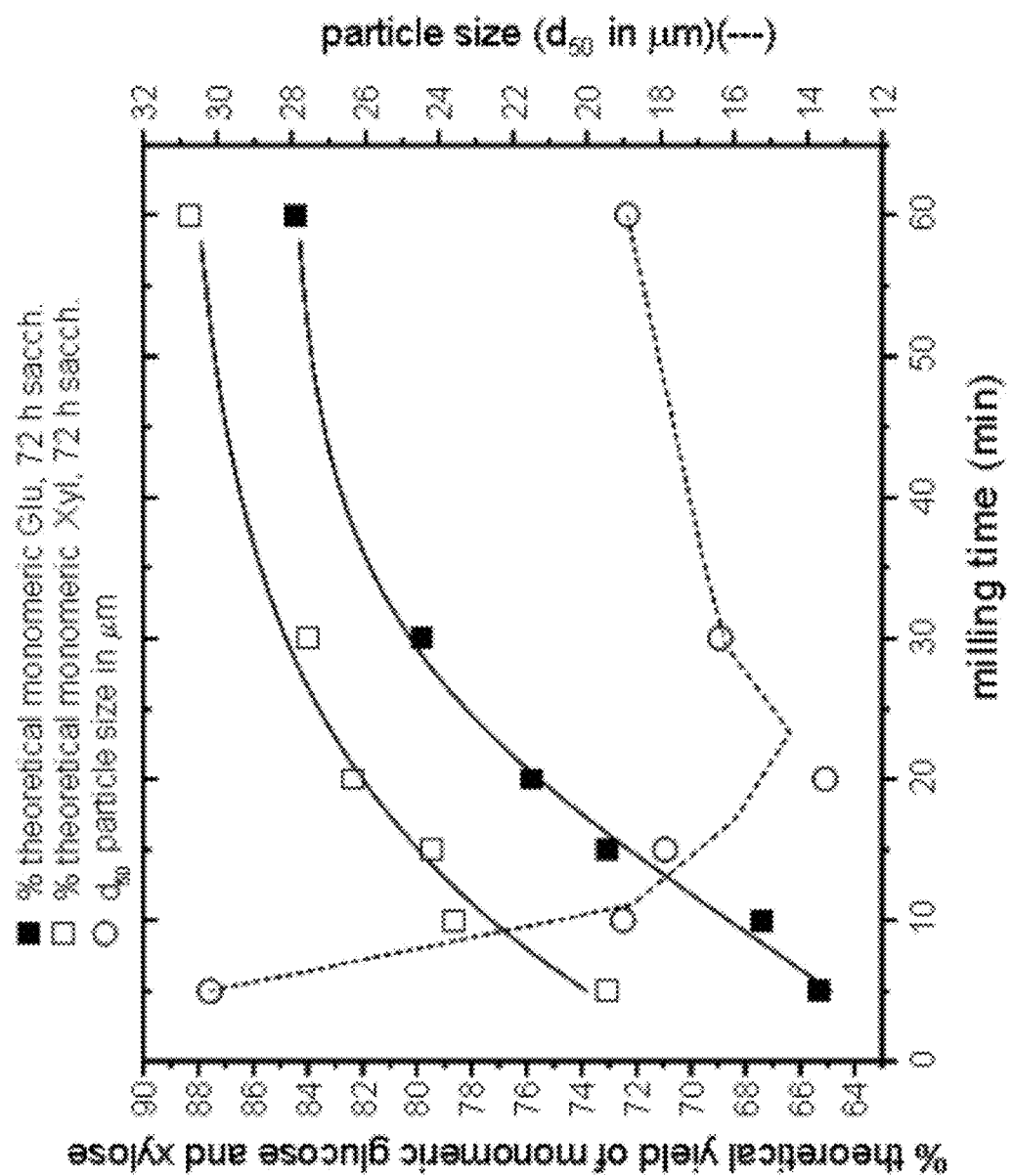
FIG. 8 shows a graph of percent of theoretical saccharification yields of monomeric glucose (Glu) and xylose (Xyl) of 1 mm knife milled fall-harvested switchgrass treated with 10 wt % anhydrous ammonia at 160° C. for 1 hour, attritor milled for different times (min) with 0.25" (0.635 cm) stainless steel beads as in FIG. 7 and saccharified for 72 h (at 14% solids loading); compared to particle size in the treated samples.

The saccharification yields initially show an inverse correlation with the particle size initially (FIG. 8) as yields first increase while particle size decreases, then in later stages yields continue to increase while particle size increases.

TABLE 4

Particle size and amorphous component of anhydrous ammonia treated switchgrass samples milled for different times.

| Anhydrous ammonia | Milling time | $d_{50}$ μm | % amorphous component |
|---|---|---|---|
| no | 0 | ~600 | 59.1 |
| yes | 0 | ~600 | 46.5 |
| yes | 5 min | 30.20 | 66.3 |
| yes | 10 min | 19.03 | 69.5 |
| yes | 15 min | 17.89 | 71.3 |
| yes | 20 min | 13.55 | 79.6 |
| yes | 30 min | 16.38 | 83.1 |
| yes | 60 min | 18.91 | 90.2 |

Example 5

Figure 9A:
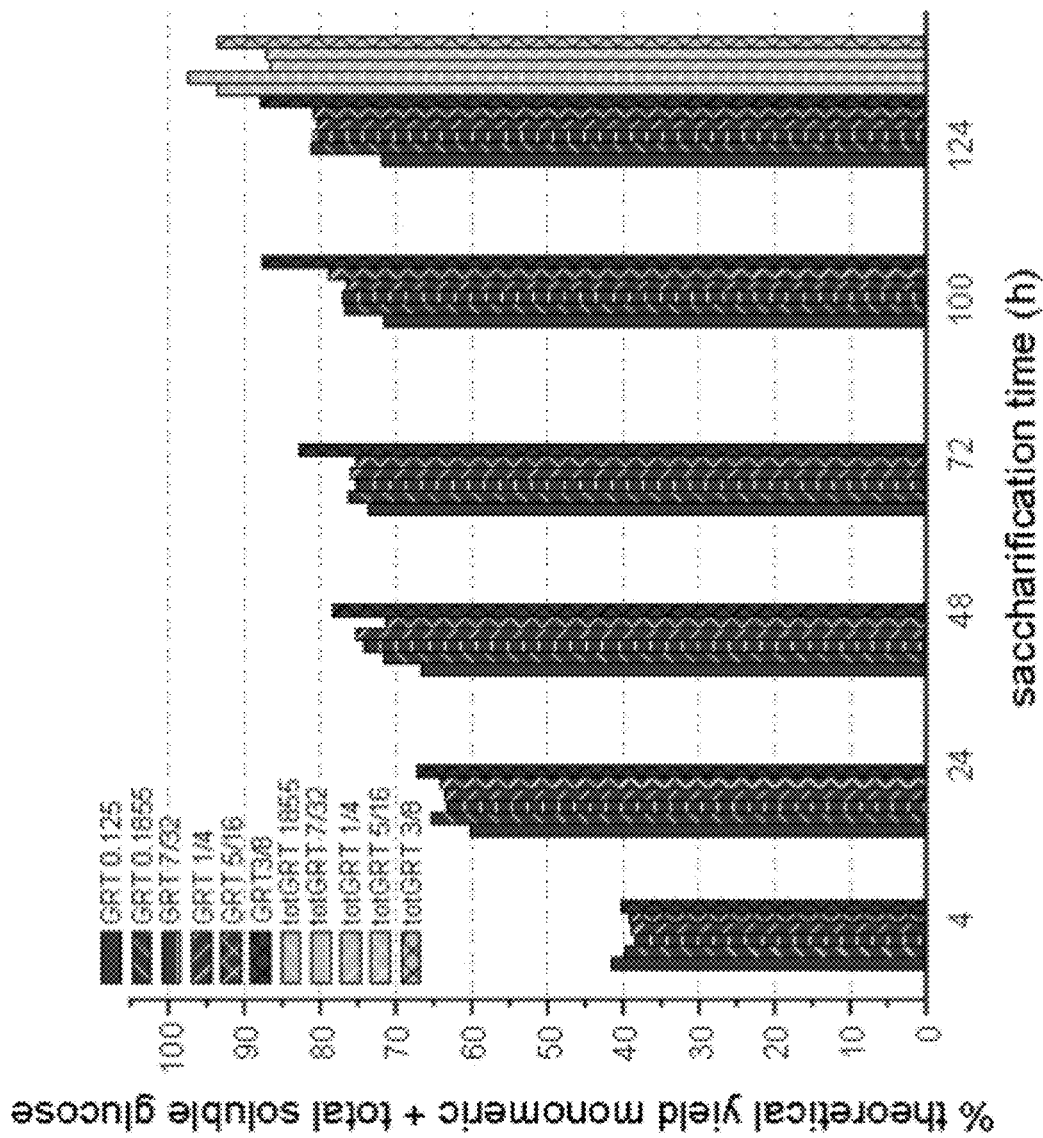
FIG. 9 shows graphs of percent of theoretical saccharification yields of glucose (G) in (A) and xylose (X) in (B) in 1 mm knife milled fall-harvested switchgrass samples treated with 20 wt % anhydrous ammonia at room temperature (RT) for 9 days and ball-milled for 5 hours with stainless steel beads of different sizes (0.125" (0.3175 cm), 0.1855" (0.471 cm), 7/32 or 0.2188" (0.556 cm), 1/4 or 0.250" (0.635 cm), 5/16 or 0.3125" (0.794 cm) and 3/8 or 0.375" (0.953 cm)) at a ratio of 200 g of beads to 5 g biomass, and then saccharified for different times (4, 24, 48, 72, 100, 124 hours), using 14% solids loading. All bars are monomeric sugars except for the last bar of each set which is the total soluble sugar yield (monomer and oligomer) for glucose in (A) and xylose in (B) at 124 h of saccharification.
Figure 10A:
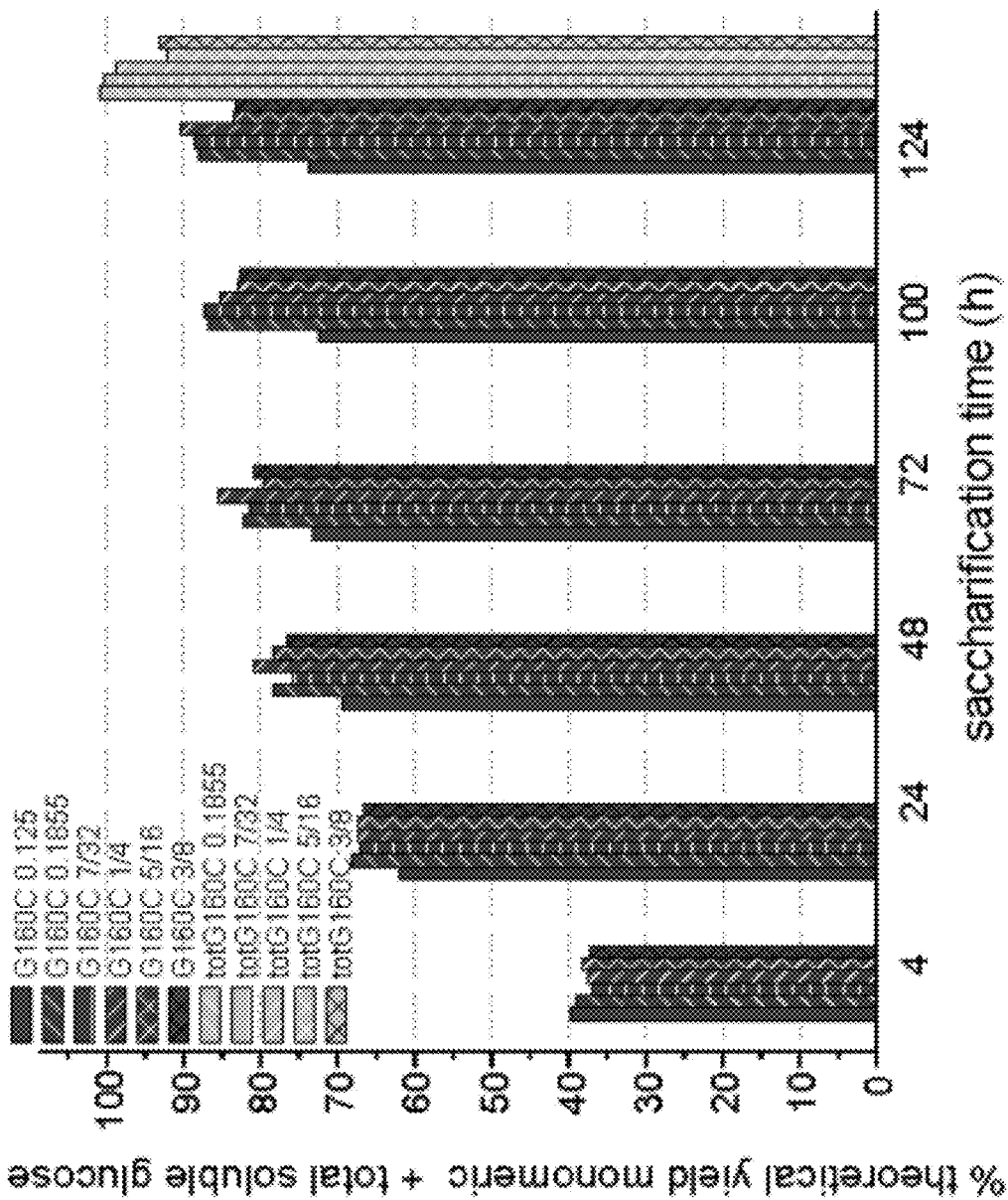
FIG. 10 shows graphs of percent of theoretical saccharification yields of glucose (G) in (A) and xylose (X) in (B) in 1 mm knife milled fall-harvested switchgrass samples treated with 10 wt % anhydrous ammonia at 160° C. for 1 hour and ball-milled for 5 hours with stainless steel beads of different sizes (0.125" (0.3175 cm), 0.1855" (0.471 cm), 7/32 or 0.2188" (0.556 cm), 1/4 or 0.250" (0.635 cm), 5/16 or 0.3125" (0.794 cm) and 3/8 or 0.375" (0.953 cm)) as in FIG. 9, and then saccharified for different times (4, 24, 48, 72, 100, 124 hours), using 14% solids loading. All bars are monomeric sugars except for the last bar of each set which is the total soluble sugar yield (monomer and oligomer) for glucose in (A) and xylose in (B) at 124 h of saccharification.
Figure 11A:
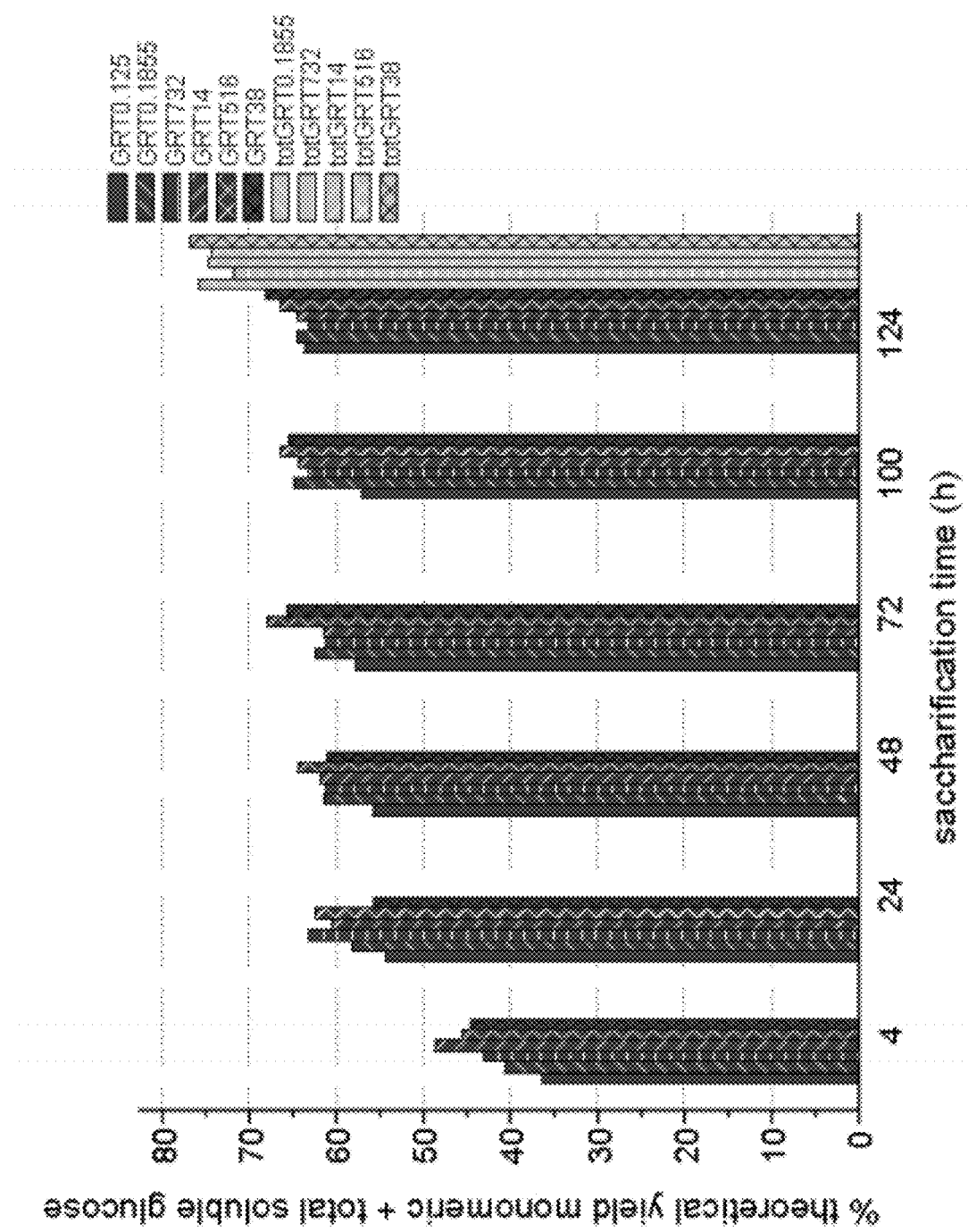
FIG. 11 shows graphs of percent of theoretical saccharification yields of glucose (A) and xylose (B) in 1 mm knife milled fall-harvested switchgrass samples pretreated with 20 wt % anhydrous ammonia at room temperature for 9 days and milled for 5 hours with stainless steel beads of different sizes (0.125" (0.3175 cm), 0.1855" (0.471 cm), 7/32 or 0.2188" (0.556 cm), 1/4 or 0.250" (0.635 cm), 5/16 or 0.3125" (0.794 cm) and 3/8 or 0.375" (0.953 cm)) as in FIG. 9, then saccharified for different times (4, 24, 48, 72, 100, 124 hours), using 25% solids loading. All bars are monomeric sugars except for the last bar of each set which is the total soluble sugar yield (monomer and oligomer) for glucose in (A) and xylose in (B) at 124 h of saccharification.
Figure 11B:
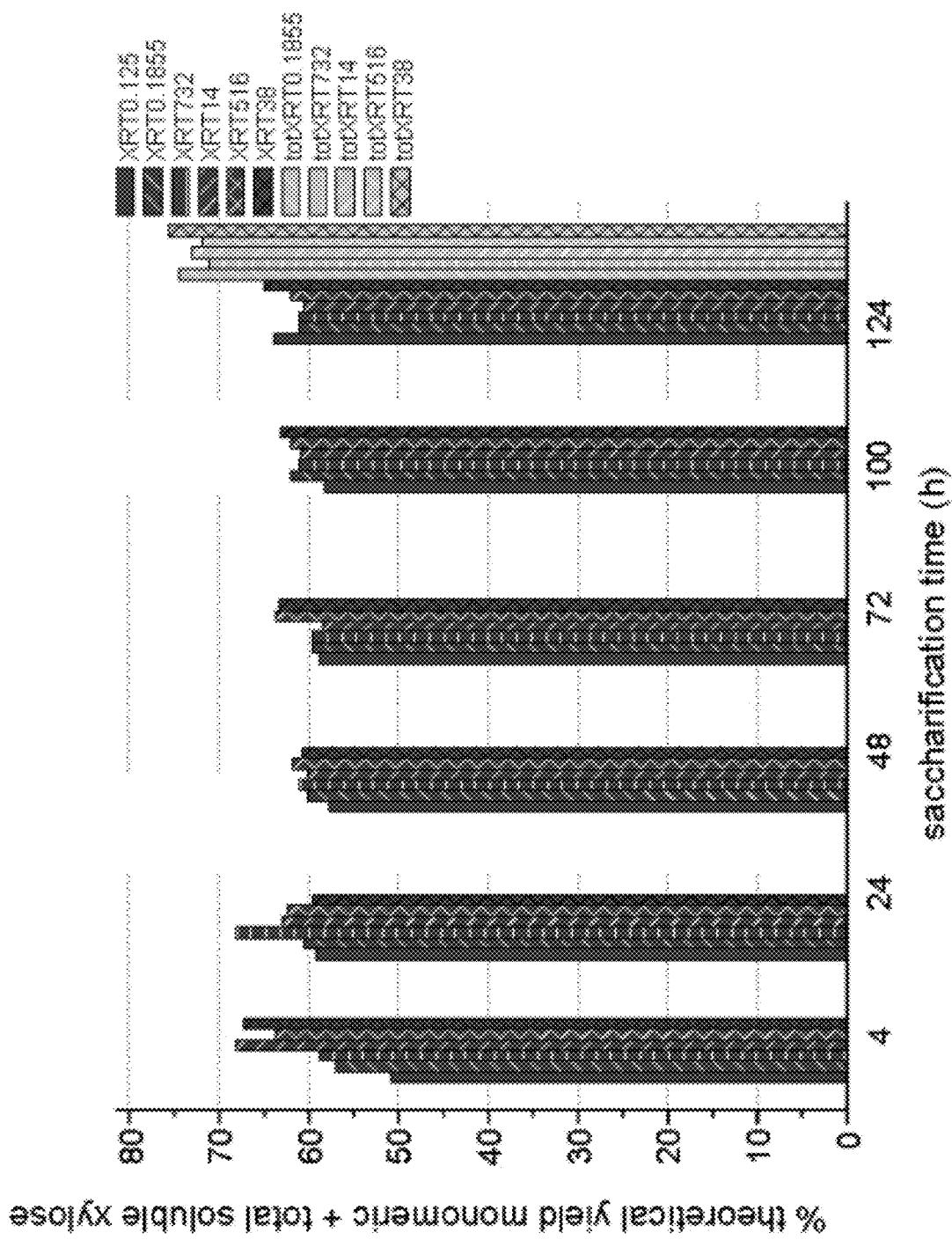
Figure 12A:
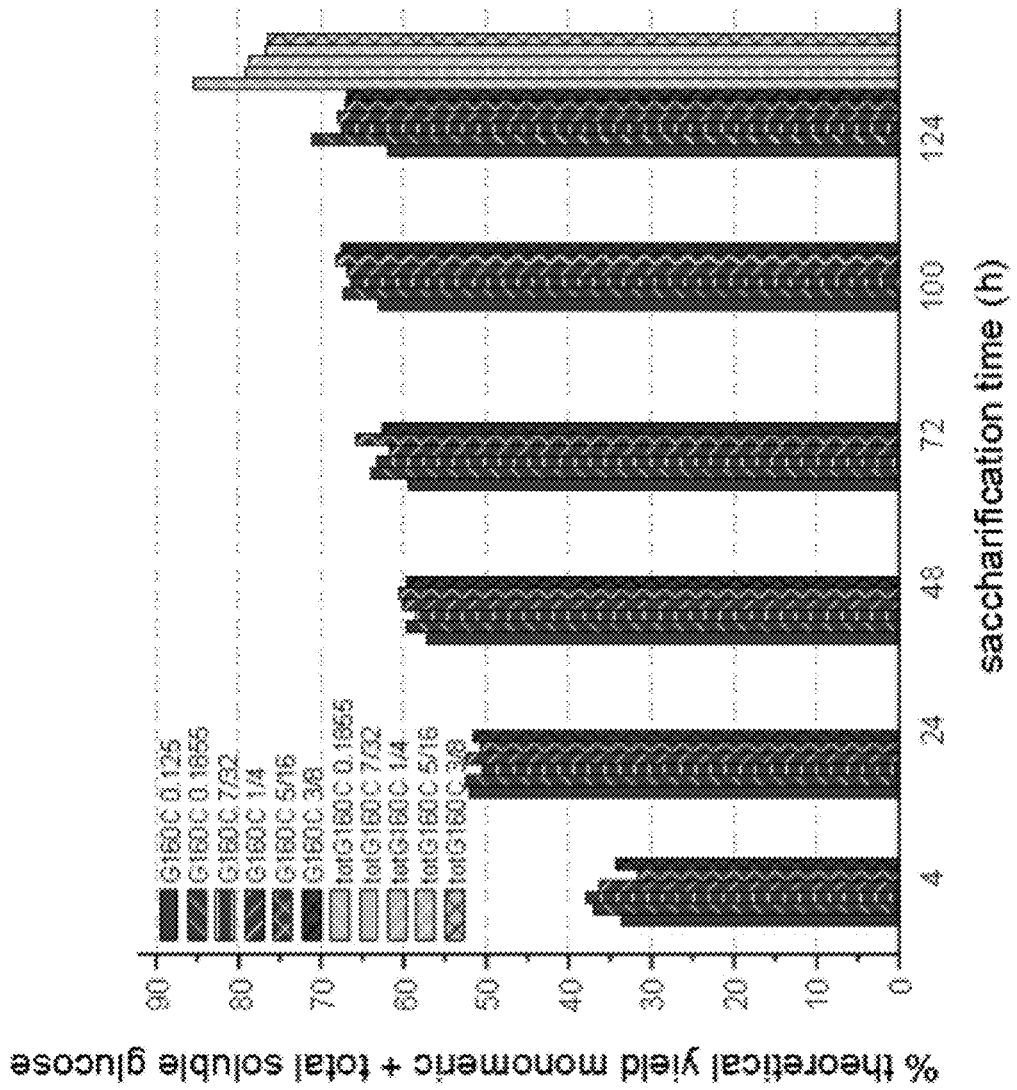
FIG. 12 shows graphs of percent of theoretical yields of glucose (A) and xylose (B) in 1 mm knife milled fall-harvested switchgrass samples treated with 10 wt % anhydrous ammonia at 160° C. for 1 hour and ball-milled for 5 hours with stainless steel beads of different sizes (0.125" (0.3175 cm), 0.1855" (0.471 cm), 7/32 or 0.2188" (0.556 cm), 1/4 or 0.250" (0.635 cm), 5/16 or 0.3125" (0.794 cm) and 3/8 or 0.375" (0.953 cm)) as in FIG. 9, then saccharified for different times (4, 24, 48, 72, 100, 124 hours), using 25% solids loading. All bars are monomeric sugars except for the last bar of each set which is the total soluble sugar yield (monomer and oligomer) for glucose in (A) and xylose in (B) at 124 h of saccharification.
Figure 12B:
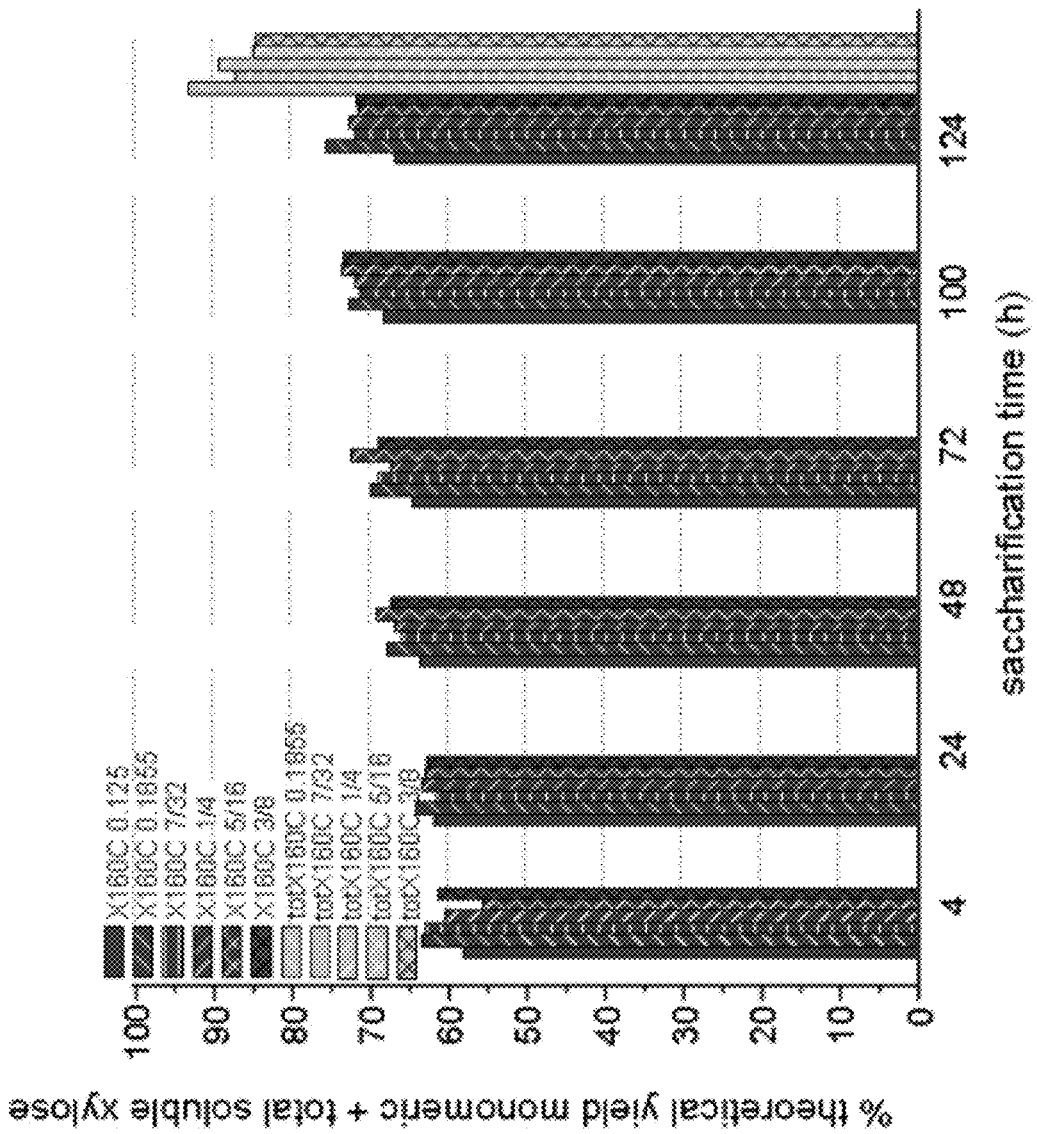

Effects of Milling Bead Size and Solids Loading in Saccharification on Sugar Yields from Biomass Pretreated with Anhydrous Ammonia and 5 Hour of Ball Milling Fall-harvested switchgrass from the same batch as used in Example 3 was treated with anhydrous ammonia at RT or at 160° C. as described in Example 3. The treated biomass was then ball-milled for 5 h with stainless steel beads of the following sizes: ⅛ or 0.125" (0.3175 cm), 0.1855" (0.471 cm), 7/32 or 0.2188" (0.556 cm), ¼ or 0.250" (0.635 cm), 5/16 or 0.3125" (0.794 cm) and ⅜ or 0.375" (0.953 cm). Five grams of biomass were milled with 200 g of stainless steel beads at 83 rpm in 125 mL plastic bottles for 5 h. Following the milling, the samples were saccharified in single batch mode as in Example 2, except that the solids loading in the saccharification was either 14% (FIGS. 9, 10) or 25% (FIGS. 11, 12). Samples were analyzed for glucose and xylose as in Example 1. In addition, after 124 h of saccharification, samples were filtered (0.2 μm) to remove the solids and the filtrate was heated at 121° C. for 1 h in the presence of 4% $H_2SO_4$. Control samples of glucose and xylose were used to correct for any sugar degradation during heating and total soluble sugar content was determined as in Example 2.

Under the milling conditions used, the 0.1855" to 0.250" (0.471 cm-0.635 cm) diameter beads gave the highest yields for the switchgrass treated with anhydrous ammonia at 160° C., while the 0.1855" (0.471 cm) and 0.375" (0.953 cm) beads seemed to confer a small advantage to the switchgrass treated with anhydrous ammonia at RT.

Generally, yields were higher with the 14% solids loading than the 25% solids loading. Generally, the 160° C. ammonia-treated switchgrass had slightly better yields than did the RT-treated switchgrass, particularly for xylose. The acid hydrolysis at the end of the saccharification indicated the presence of a significant amount of soluble oligomeric sugar, which is likely to be converted to monomers and for use in fermentation.

Example 6

Figure 13:
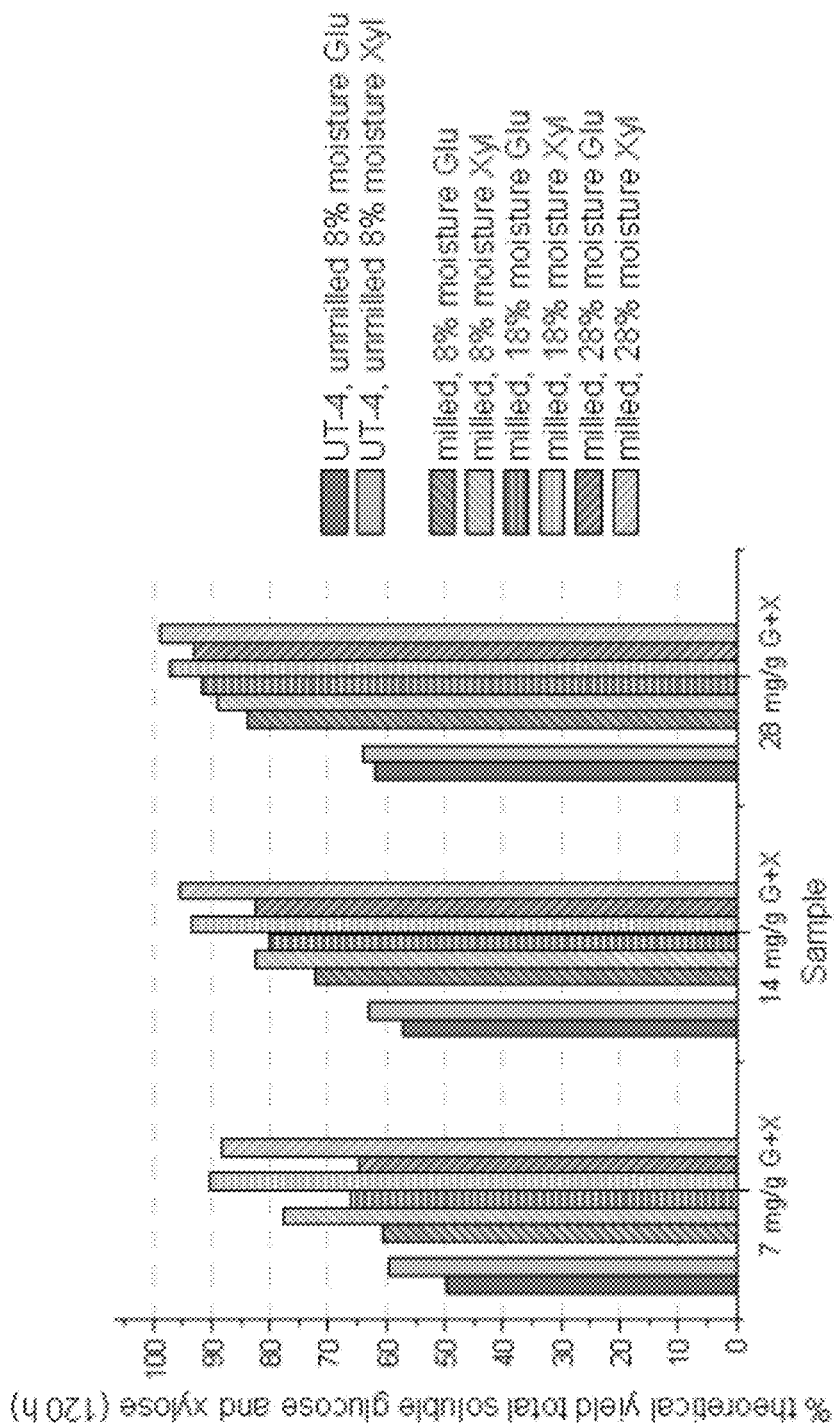
FIG. 13 shows a graph of percent of theoretical yields of total soluble glucose and xylose in 1 mm knife milled switchgrass samples containing 8%, 18%, or 28% moisture treated with 10 wt % anhydrous ammonia at 150-160° C. for 1 hour and attritor milled for 5 min, then sacharified for 120 hr using 25% solids loading in different amounts of enzymes.

Influence of Biomass Moisture Content on the Efficacy of the Anhydrous Ammonia Treatment Prior to Attritor Milling The moisture content of samples of 1 mm knife-milled switchgrass was adjusted to 8% (92% DM), 18% (82% DM), or 28% (72% DM) moisture content and subjected to 10% anhydrous ammonia treatment for 1 h at 150-160° C. The samples had dry matter contents of approximately 98%, 97% and 96%, respectively, after flashing off of the ammonia at the end of the anhydrous ammonia treatment. The samples were attritor milled for the equivalent of 5 min in the Union Process attritor mill of Example 4. The samples were then saccharified for 120 hr at 47° C. at a solids loading of 25% at enzyme loadings of 7, 14 and 28 mg glucanase+xylanase/g glucan+xylan. Yields of total soluble glucose and sylose (includes monomers and olibomers) are shown in FIG. 13. The 7 and 14 mg enzyme loadings showed an absolute increase in solubilized xylose yield of 12% and 11%, respectively, for samples ammonia treated at 18% moisture as opposed to 8% moisture content. The absolute increases in solubilized glucose yields were 5.5% and 8% for the same samples. The 18% and 28% moisture content samples produced similar saccharification yields for glucose and xylose. There was therefore a distinct advantage to having a moisture content of at least 18% going into the anhydrous ammonia treatment.

What is claimed is:

1. A process for producing readily saccharifiable biomass comprising:
    a) providing lignocellulosic biomass;
    b) contacting the biomass of (a) with anhydrous ammonia to produce ammonia-treated biomass; and
    c) disrupting the ammonia-treated biomass of (b) by applying mechanical energy through a mechanical disruption means to produce a pretreated biomass which is readily saccharifiable;
    wherein the pretreated biomass comprises an amorphous cellulose component and;
    wherein the percentage of the amorphous cellulose component in the pretreated biomass is higher as compared with the percentage of the amorphous cellulose component in a pretreated biomass not contacted with anhydrous ammonia and disrupted with the same level of mechanical energy as in (c).

2. The process according to claim 1 wherein the pretreated biomass of step c) has a particle size of less than about 0.1 mm.

3. The process according to claim 1 wherein the energy required for the mechanical disruption of step (c) is about 4 to about 10 fold less as compared with the energy required for mechanical disruption of a lignocellulosic biomass not contacted with anhydrous ammonia.

4. The process according to claim 1 wherein, upon saccharification, the pretreated biomass of step c) produces fermentable sugars at a higher rate when compared with a pretreated biomass that is not contacted with anhydrous ammonia and is disrupted as in (c).

5. The process of claim 1 wherein the ammonia-treated biomass is substantially dry following ammonia pretreatment.

6. The process of claim 1 wherein the mechanical disruption means is selected from the group consisting of a means for: pounding, grinding, shearing, crushing, and combinations thereof.

7. The process of claim 1 wherein the mechanical disruption means is a means selected from the group consisting of: attritor milling, hammer milling, ball milling, bead milling, vibratory ball milling, vibratory rod milling, jet milling, pin milling, turbine milling, air classifier milling, roll milling and planetary ball milling.

8. The process of claim 1 wherein steps (b) and (c) occur concurrently.

9. The process of claim 1 wherein the disruption occurs over a period of less than 2 days.

10. The process of claim 9 wherein the disruption occurs over a period of less than 60 minutes.

11. The process of claim 1 wherein the anhydrous ammonia of step (b) is at a concentration that is between about 2 and about 30 weight percent relative to dry weight of lignocellulosic biomass.

12. The process of claim 11 wherein anhydrous ammonia is at a concentration of between about 10 and about 25 weight percent relative to dry weight of lignocellulosic biomass.

13. The process of claim 1 wherein the lignocellulosic biomass of step (b) is in contact with anhydrous ammonia for a period of about thirty minutes to about one year.

14. The process of claim 1 wherein the lignocellulosic biomass of step (b) attains a moisture content of about 15% and about 30% prior to the application of mechanical energy.

15. The process of claim 1 wherein the lignocellulosic biomass of step (b) is contacted with anhydrous ammonia at a temperature that is between about 0° C. and about 200° C.

16. The method of claim 1 wherein lignocellulosic biomass of (a) is selected from the group consisting of corn cobs, corn husks, corn stover, grasses, wheat straw, barley straw, hay, rice straw, switchgrass, waste paper, sugar cane bagasse, sorghum bagasse or stover, soy stover, components obtained from milling of grains, trees, branches, roots, leaves, wood chips, sawdust, shrubs, bushes, vegetables, fruits, flowers, animal manure, and a combination thereof.

* * * * *